(12) United States Patent
O'Keefe

(10) Patent No.: US 9,057,063 B2
(45) Date of Patent: Jun. 16, 2015

(54) GENETICALLY MODIFIED BIOLOGICAL CELLS

(75) Inventor: Theresa O'Keefe, Waltham, MA (US)

(73) Assignee: Theresa O'Keefe, Waltham, MA (US)

( * ) Notice: Subject to any disclaimer, the term of this patent is extended or adjusted under 35 U.S.C. 154(b) by 1044 days.

(21) Appl. No.: 12/596,345

(22) PCT Filed: Apr. 21, 2008

(86) PCT No.: PCT/US2008/061060
§ 371 (c)(1),
(2), (4) Date: Aug. 20, 2010

(87) PCT Pub. No.: WO2008/131359
PCT Pub. Date: Oct. 30, 2008

(65) Prior Publication Data
US 2010/0304432 A1    Dec. 2, 2010

Related U.S. Application Data

(60) Provisional application No. 60/913,043, filed on Apr. 20, 2007, provisional application No. 60/947,757, filed on Jul. 3, 2007.

(51) Int. Cl.
*C12N 15/03* (2006.01)
*C12P 19/42* (2006.01)
*C07K 14/195* (2006.01)
*C12N 15/70* (2006.01)
*C12N 15/74* (2006.01)
*A61K 38/00* (2006.01)

(52) U.S. Cl.
CPC ............ *C12N 15/03* (2013.01); *C12P 19/42* (2013.01); *C12N 2500/38* (2013.01); *C07K 14/195* (2013.01); *C12N 15/70* (2013.01); *C12N 15/74* (2013.01)

(58) Field of Classification Search
CPC ...................................... C12N 15/03
See application file for complete search history.

(56) References Cited

U.S. PATENT DOCUMENTS

| 7,785,861 | B2* | 8/2010 | Devroe et al. ............. 435/252.3 |
| 2004/0091860 | A1* | 5/2004 | Ohashi et al. ............. 435/6 |
| 2004/0221330 | A1* | 11/2004 | Klimyuk et al. ............. 800/278 |
| 2005/0227326 | A1* | 10/2005 | Taron et al. ............. 435/69.1 |
| 2009/0203070 | A1* | 8/2009 | Devroe et al. ............. 435/69.1 |
| 2010/0291651 | A1* | 11/2010 | Xu et al. ............. 435/168 |

OTHER PUBLICATIONS

Roth et al. (1993) Characterization of the Cobalamin (Vitamin B12) Biosynthetic Genes of *Salmonella typhimurium*, J. Bacteriol., vol. 175, No. 11, pp. 3303-3316.*
Richardson et al. (1997) Integration of heterologous plasmid DNA into multiple sites on the genome of *Campylobacter coli* following natural transformation, J. Bacteriol., vol. 179, No. 5, pp. 1809-1812.*
Shearer et al. (1999) Anaerobic Growth of *Paracoccus denitrificans* Requires Cobalamin: Characterization of cobK and cobJ Genes, J. Bacteriol., vol. 181, No. 22, pp. 6907-6913.*
Vioque, A (2007) "Transgenic Microalgae as Green Cell Factories", Ed. by Leon et al., Landes Bioscience and Springer Science & Business Media, Chapter 2, pp. 12-22.*
Huang et al. (2002) Proteomics of Synechocystis sp. Strain PCC 6803, Mol. Cell. Proteomics, VOI. 1, pp. 956-966.*
Reference (2014) "Cobalamin (vitamin B12) biosynthesis CobM/CbiF, precorrin-4 C11-methyltransferase", www.ebi.ac.uk/interpro/entry/IPR006362, pp. 1-3.*

* cited by examiner

*Primary Examiner* — Maryam Monshipouri
*Assistant Examiner* — Samuel Liu
(74) *Attorney, Agent, or Firm* — Pepper Hamilton LLP

(57) ABSTRACT

The present invention is based, in part, on our discovery of a way to configure expression cassettes so that the expression of a selectable marker protein, which is critical for the growth or survival of a cell, also results in the expression of a protein of interest in a biological cell. Accordingly, in one aspect, the invention features a genetically modified cell (e.g., a bacterial cell) that includes a chromosomally integrated or cytoplasmic expression cassette that includes a first nucleic acid sequence encoding a protein of interest and a second nucleic acid sequence encoding a selectable marker protein. The regulatory sequence (e.g., the sequence encoding a functional promoter) that drives expression of the required selectable marker protein also drives expression of the protein of interest. For that reason, we may refer to their expression as being "linked" or "functionally couple."

11 Claims, 23 Drawing Sheets

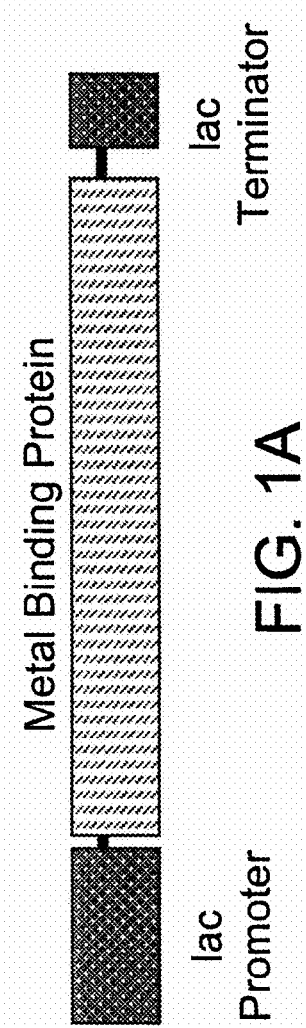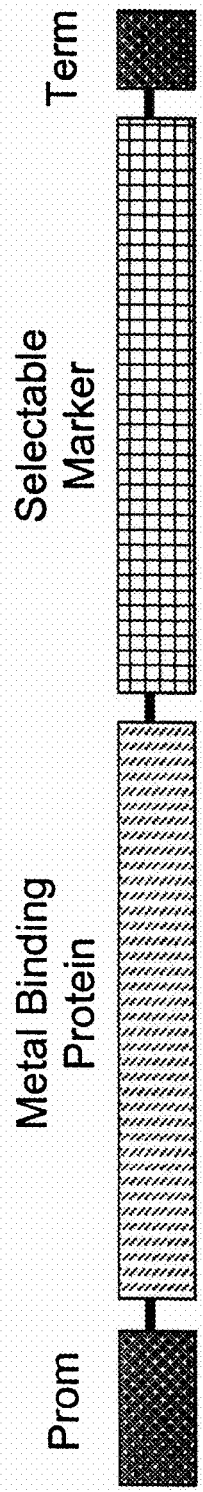

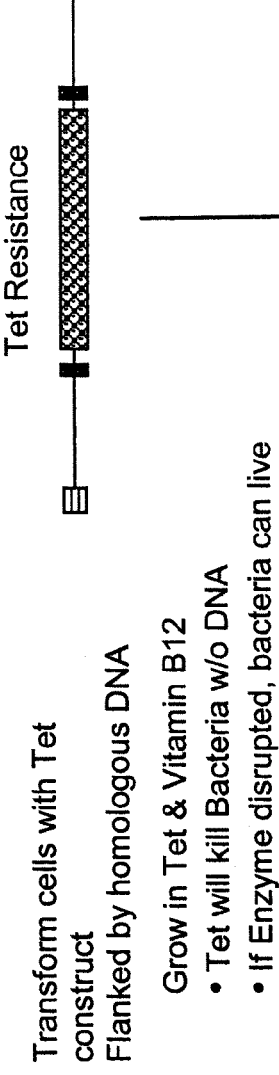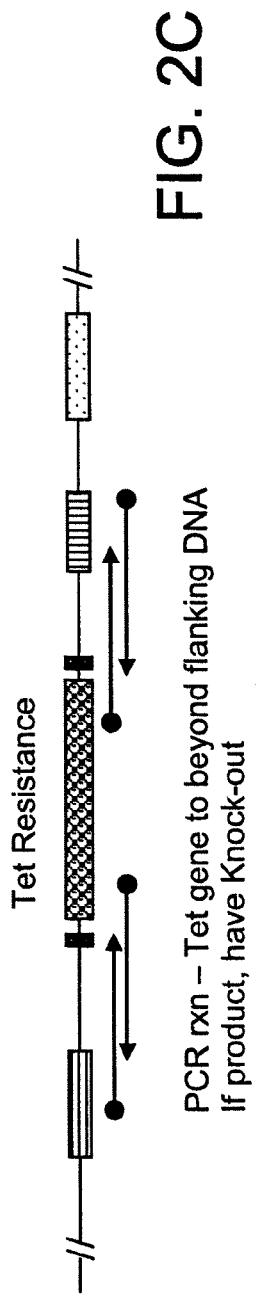

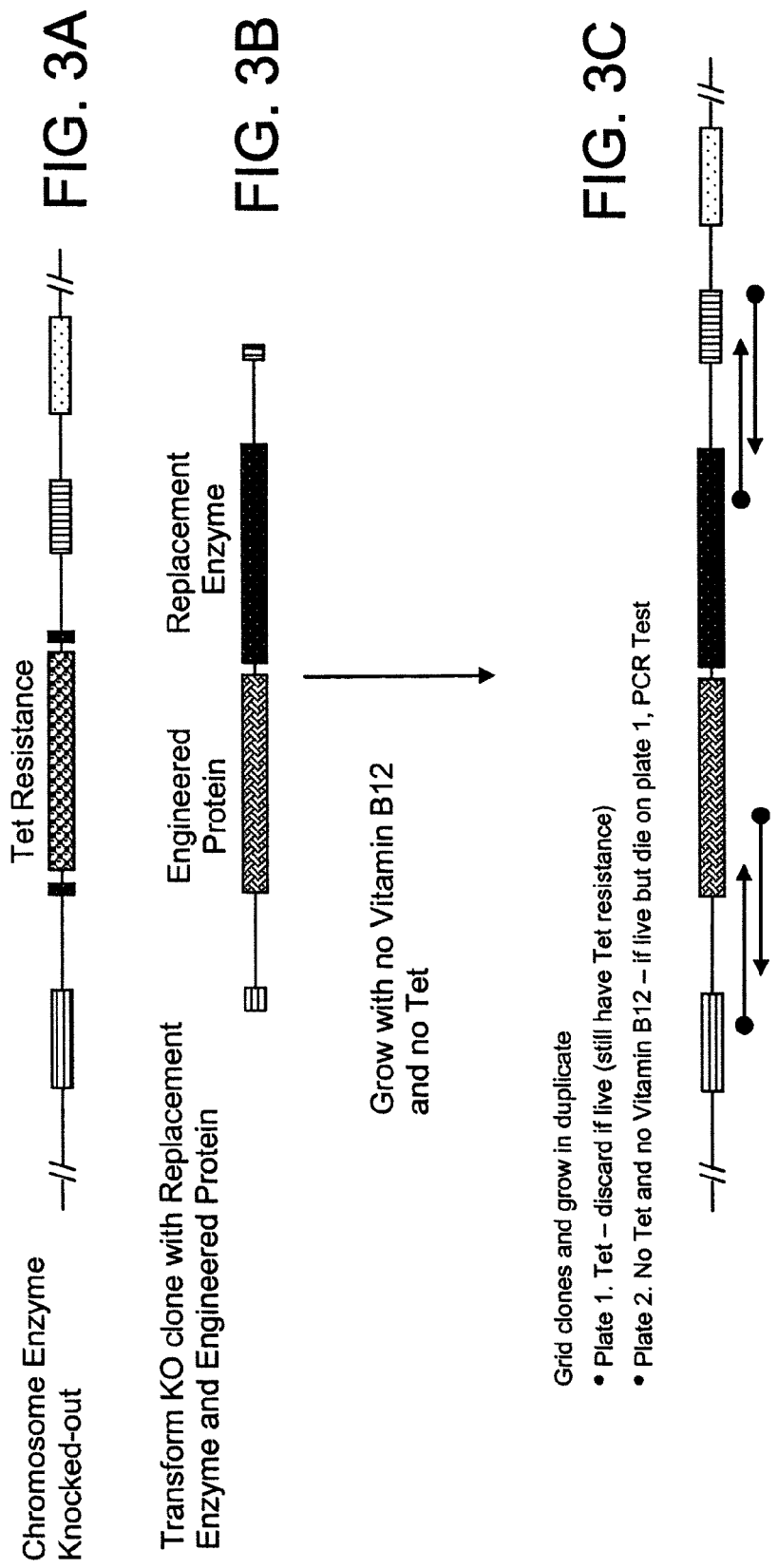

| | | Uroporphyrinogen III | |
|---|---|---|---|
| | | CobA (EC 2.1.1.107) | |
| | syc1242c | Precorrin-2 | |
| | | | *Oxygen Independent Pathway* |
| | | | CobA/CysG (EC 1.3.1.76) | syc1500_d |
| | | | Sirohydrochlorin |
| | | | CbiK/CbiX (EC 4.99.1.3) | Synpcc7942_2611 |
| | | | Co-Precorrin-2 |
| | | | CbiL (EC 2.1.1.151) | unknown |
| | | | Co-Precorrin-3 |
| *Oxygen Dependent Pathway* | | | |
| syc2241_c | CobI (EC 2.1.1.130) | | |
| | Precorrin-3A | | |
| syc2243_c | CobG (EC 1.14.13.83) | | |
| | Precorrin-3B | | |
| GYMAORF1594 / GYMAORF1848 | CobJ (EC 2.1.1.131) | | CbiH (EC 2.1.1.131) | GYMAORF1594 / GYMAORF1848 |
| | Precorrin-4 | | Co-Precorrin-4 |
| syc0321_d | CobM (EC 2.1.1.133) | | CbiF (EC 2.1.1.133) |
| | Precorrin-5 | | Co-Precorrin-5a |
| unknown | CobF (EC 2.1.1.152) | | CbiD (EC 2.1.1.-) | unknown |
| | Precorrin-6a | | Co-Precorrin-6a |
| syc1476_d | CobK (EC 1.3.1.54) | | CbiJ (EC 1.3.1.54) |
| | Precorrin-6b | | Co-Precorrin-6b |
| unknown | CobL (EC 2.1.1.132) | | CbiE/CbiT (EC 2.1.1.132) | unknown |
| | Precorrin-8X | | Co-Precorrin-8X |
| GYMAORF0462 / GYMAORF1578 | CobH (EC 5.4.1.2) | | CbiC (EC 5.4.1.2) | GYMAORF0462 / GYMAORF1578 |
| | Hydrogenobyrinic acid | | Cobyrinic acid |
| GYMAORF1192 | CobB (EC 6.3.5.9) | | CbiA (EC 6.3.1.-) |
| | Hydrogenobyric acid a,c, diamide | | |
| syc1407_d | CobN (EC 6.6.1.2) | | |

FIG. 5A

Text Legend

Black — Product
EC — Enzyme Commission #
Blue/Bold — Enzyme Name
*Green/Italic* — Gene Locus

| Pathway Overlap | |
|---|---|
| | Cob(II)yrinic acid a,c-diamide |
| *Tery_4461* | Cob(II)yrinic acid a,c-diamide reductase (EC 1.16.8.1) |
| | Cob(I)yrinic acid a,c-diamide |
| *GYMAORF1191 / GYMAORF1208* | CobO/CobP/BtuR (EC 2.5.1.17) |
| | Adenosyl-Cobyinate a,c-diamide |
| *GYMAORF2683* | CobQ/CbiP (EC 6.3.5.10) |
| | Adenosyl-Cobyrinate hexamide |
| *GYMAORF0425* | CobC/CobD/CbiB (EC 6.3.1.10) |
| | Adenosyl-Cobinsamide |
| *unknown* | CobP/CobU (EC 2.7.1.156/EC 2.7.7.62) |
| | Adenosyl-Cobinsamide-phosphate |
| *unknown* | CobP/CobU (EC 2.7.1.156/EC 2.7.7.62) |
| | Adenosyl-GDP-Cobinamide |
| *GYMAORF2411* | CobV/CobS (EC 2.7.8.26) |
| | Adenosyl-Cobalamin (vitamin B12 coenzyme) |

FIG. 5B

| PCC | Name | Sect | N2 fixation | Salt Tolerance | Nutrition | Date of sample | Source |
|---|---|---|---|---|---|---|---|
| 6712 | Chroococcidiopsis | II | anaerobic | euryhaline | chemoheterotroph | 1967 | water sample, reservoir, Marin County, California, U.S.A./ very slow growing |
| 7004 | Leptolyngbya | III | anaerobic | ? | chemoheterotroph | 1962 | mangrove root, Lydia Ann Channel, Port Aransas, Texas, U.S.A. |
| 7104 | Leptolyngbya | III | anaerobic | euryhaline | chemoheterotroph | 1960 | rock at shoreline, Montauk Point, Long Island, New York, U.S.A. |
| 7111 | Calothrix | IV | aerobic | euryhaline | chemoheterotroph | 1970 | hemispherical macroscopic colony, intertidal zone, Bodega, California, U.S.A. |
| 7116 | Calothrix | IV | aerobic | Marine | chemoheterotroph | 1968 | La Paz, Baja California, U.S.A. |
| 73104 | Nodularia | IV | aerobic | ? | chemoheterotroph | | alkaline soil, Spotted Lake, British Columbia, Canada |
| 7416 | Nostoc | IV | aerobic | ? | chemoheterotroph | 1972 | shallow pool, San Andreas valley, California, U.S.A. |
| 7601/1 | Tolypothrix | IV | aerobic | ? | chemoheterotroph | | Derivative of 7601 (fresh water sample, Yale, U.S.A. |

FIG. 6

| Subject | Invention | Genes for Enzymes/Proteins | Accession or E.C.# |
|---|---|---|---|
| Fructose Transport | create cyanobacteria with accelerated cross membrane fructose transportation | Phosphoenolpyruvate-protein phosphotransferase | EC 2.7.3.9 |
| | | HPr protein | Protein CAD10220 |
| | | protein-Nπ-phosphohistidine- sugar phosphotransferase (fructose-specific) | EC 2.7.1.69 |
| Fructose to Pyruvate | create cyanobacteria with accelerated metabolism of fructose | Hepatic fructokinase | EC 2.7.1.3 |
| | | Aldolase B | EC 4.1.2.13 |
| | | Glyceraldehyde kinase | EC 2.7.1.28 |
| Production of Zein | Create cyanobacteria that produce the corn storage protein Zein | Zein | Protein CAA32512 |

FIG. 7A

| Subject | Invention | Genes for Enzymes/Proteins | Accession or E.C.# |
|---|---|---|---|
| Production of Fatty Acid | create cyanobacteria with accelerated biosynthesis of fatty acids | *Genes of pyruvate dehydrogenase complex* | |
| | | pyruvate dehydrogenase (acetyl-transferring) | EC 1.2.4.1 |
| | | dihydrolipoyl dehydrogenase | EC 2.3.1.12 |
| | | dihydrolipoyllysine-residue acetyltransferase | EC 1.8.1.4 |
| | | *Fatty Acid synthesis* | |
| | | Acetyl-CoA Carboxylase | EC 6.4.1.2 |
| | | Malonyl-CoA:ACP transacylase | EC 2.3.1.39 |
| | | acyl carrier protein (ACP) | Gene acpP |
| | | Fatty Acid Synthase (animal) | EC 2.3.1.85 |
| Destroying VOCs | create cyanobacteria that destroy VOCs including Acetate (vinegar), Propanoate (old sweat) or Butyrate (rancid butter) | Propinate-CoA Transferase (Propanoate destruction) | EC 2.8.3.1 |
| | | Acetate-CoA Ligase (Acetate destruction) | EC 6.2.1.13 |
| | | Butanal Dehydrogenase (Butyrate destruction) | EC 1.2.1.57 |
| Glycerol to Pyruvate | create cyanobacteria with accelerated metabolism of glycerol | Glycerol kinase | EC 2.7.1.30 |
| | | Glycerol 3-phosphate dehydrogenase | EC 1.1.1.8 |
| Lactic Acid to Pyruvate | create cyanobacteria with accelerated conversion of lactic acid to pyruvate | Lactate Dehydrogenase M4 | EC 1.1.1.27 |

FIG. 7B

Pantothenate (Vitamin B5) Enzymes
Only prokaryote (bacteria)

ilvB
ilvC
ilvD
panB
panE
panC

Coenzyme A Enzymes
Prokaryote and Eukaryote
(bacteria, plants, animals)

coaA
coaBC
coaD
coaE

Enzyme for Activating APC
Prokaryote and Eukaryote
(bacteria, plants, animals)
holo-ACP synthase

FIG. 19

NM_001112761 – *Zea mays* (corn) – Zein (SEQ ID NO:___)

DNA Sequence

```
  1 ATGGCTACCA AGATATTAGC CCTCCTTGCG CTTCCTTGCC TTTTAGTGAG CGCAACAAAT
 61 GCGTTCATTA TCCACAGTG CAATGGGTTT CCTAGTGCCA GTATTCCACA GTTCCTCCCA
121 CCAGTTACTT CAATGGGTTT CGAACATCCA GCCGTGCAAG CCTACAGGCT ACAACTAGCG
181 CTTGCGGCGA GCGCCTTACA ACAACCAATT GCCCAATTGC AACAACAAAC CTTGGCACAT
241 CTAACCCTAC AAACCATTGC TGGTGAACCC TGTCACCTAC AGTTTCTGCC ATCACTGAGC
301 CACCTAGCCA TGGTGAACCC TGTCACCTAC TTGCAACAGC AGCTGCTTGC ATCCAACCCA
361 CTTGCTCTGG CGAACGTAGC TGCATACCAG CAACAACAAC AGCTGCAACA GTTTATGCCA
421 GTGCTCAGTC AACTAGCCAT GGTGAACCCT GCCGTCTACC TACAACTACT TTCATCTAGC
481 CCGCTGCGG TGGGCAATGC CTACAACGTAC CTACAACAAC AGTTGCTGCA ACAAATTGTA
541 CCAGTCTGA CTCAGCTAGC TGTGCAAAC CCTGCTGCCT ACTTACAACA GTTGCTTCCA
601 TTCAACCAAC TGGCTGTGTC AAACTCTGCT GCGTACCTAC AACAGGACA ACAGTTACTT
661 AATCCATTGG CAGTGCAGTTA CCCATTGGTC GCTACCTTCC TGCAGCAGCA ACAACAATTG
721 CTGCCATACA ACCAGTTCTC TTTGATGAAC CCTGCCTTGC AGCAACCCAT CGTTGGAGGT
781 GCCATCTTT AG
```

Protein Sequence

```
  1 MATKILALLA LLALLVSATN AFIIPQCSLA PSASIPQFLP PVTSMGFEHP AVQAYRLQLA
 61 LAASALQQPI AQLQQQSLAH LTLQTIATQQ QQQQFLPSLS HLAMVNPVTY LQQQLLASNP
121 LALANVAAYQ QQQLQQFMP VLSQLAMVNP AVYLQLLSSS PLAVGNAPTY LQQLLQQIV
181 PALTQLAVAN PAAYLQQLLP FNQLAVSNSA AYLQQRQQLL NPLAVANPLV ATFLQQQQL
241 LPYNQFSLMN PALQQPIVGG AIF
```

FIG. 20

EU266533 - *Triticum aestivum* (bread wheat) - high molecular weight glutenin subunit (SEQ ID NO:__)

```
DNA Sequence
   1 ATGGCTAAGC GGTTGGTCCT CTTTGCGGCA GTAGTCATCG CCCTCGTGGC TCTCACCACC
  61 GCTGAAGGTG AGGCCTCTAG GCAACTACAG TGTGAGCACG AGCTCCAGGA GAGCTCGCTT
 121 GAGGCATGCC GGCAGGTCGT GGACCAACAG TTGGCCGGTC GGCTGCCATG GAGCACGGGG
 181 CTCCAGATGC GATGCTGCCA GCAGCTCCGA GATGTTAGCG CCAAGTGCCG CTCTGTCGCC
 241 GTCAGCCAAG TCGCAAGACA TATGAGCAA ACTGTGGTGC CGCCCAAGGG CGGATCCTTC
 301 TACCCTGGTG AGACCACGCC ACTGCAGCAA CTCCAACAAG GAATATTTTG GGGAACATCT
 361 TCACAAACAG TACAAGGGTA TTACCCAAGC GTAACTTCTC CTCGGCAGGG GTCATATTAT
 421 CCAGGCCAAG CTTCTCCACA ACAGCCAGGA CAAGGGCAAC AGCCTGGCAA ATGGCAAGAA
 481 CCAGGACAAG GCAACAATG GTACTACCCA ACTTCTCTGC AGCAGCCAGG ACAAGGGCAA
 541 CAGATAGGAA AAGGGAAACA AGGGTACTAC CCAACTTCTC TGCAGCAACC AGGACAAGGG
 601 CAACAAATAG GACAAGGGCA ACAAGGGTAC TACCCAACTT CTCCGCAGCA CACAGGACAA
 661 AGGCAACAAC CAGTACAAGG GCAACAAATA GGACAAGGGC AACAACCAGA ACAAGGGCAA
 721 CAACCAGGAC AATGGCAACA AGGGTACTAT CCAACTTCTC CACAGCAGCT AGGACAAGGG
 781 CAACAACCAG GACAATGGCA ACAATCAGGA CAAGGGCAAC AAGGGCACTA CCCAACTTCT
 841 CTACAACAGC CAGGACAAGG GCAACAAGGG CATTACCTAG CTTCTCAGCA GCAGCCAGCA
 901 CAAGGGCAAC AAGGGCACTA CCCAGCTTCT CAGCAGCAGC CAGGACAAGG GCAACAAGGG
 961 CACTACCCAG CTTCTCAGCA GCAGCCAGGA CAAAGGCAAC AAGGGCACTA CCCAGCTTCT
1021 CAGCAGCAGC CAGGACAAGG GCAACAAGGG CACTACCCAG CTTCTCAGCA GAGCCAGGA
1081 CAGGGGCAAC AAGGGCAAAT CCCAGCTTCT CAGCAGCAGC CAGGACAAGG GCAACAAGGG
1141 CACTACCCAG CTTCTCTGCA GCAACCAGGA CAACAAGGGC ATTACCCAAC TTCTCTACAG
1201 CAGCTAGGAC AAGGGCAACA AATAGGACAG CCAGGACAAA AGCAACAACC AGGACAAGGG
1261 CAACAAACAG GACAAGGGCA ACAGCCAGAA CAAGAGCAAC AACCAGGACA AGGGCAACAA
1321 GGATACTATC CAACTTCTCT GCAGCAGCCA GGACAAGGAC AACAGCAAGG ACAAGGGCAA
1381 CAAGGGTACT ACCCAACTTC TCTCCAGCAG CCAGGACAAG GCAACAAGG GCACTACCCA
1441 GCTTCTCTGC AGCAGCCAGG ACAAGGACAG CCAGGACAAA GGCAACAACC AGGACAAGGG
1501 CAACATCCAG AACAAGGGCA ACAACCAGGA CAAGGGCAAC AAGGGTACTA TCCAACTTCT
1561 CCACAGCAGC CAGGACAAGG GCAACAACTA GGACAAGGGC AACAAGGGTA CTACCCAACT
1621 TCTCCGCAGC AGCCAGGACA AGGGCAACAA CCAGGACAAG GCAACAAGG GCACTGCCCA
1681 ATGTCCCCGC AGCAGACAGG ACAAGCGCAA CAACTAGGAC AAGGCCAACA AATAGGACAA
1741 GTGCAACAAC CAGGACAAGG GCAACAAGGG TACTACCCAA CTTCTCTGCA GCAGCCTGGA
1801 CAAGGGCAAC AGTCAGGACA AGGGCAACAG TCAGGACAAG GACACCAACC AGGACAAGGG
1861 CAGCAATCAG GACAAGAGAA ACAAGGCTAC GACAGCCCAT ACCATGTTAG CGCAGAGCAG
1921 CAAGCGGCCA GCCCAATGGT GGCAAAGGCG CAGCAGCCCG CGACACAGCT GCCGACAGTG
1981 TGTCGGATGG AGGGGGCGA CGCATTGTCG GCTAGCCAGT GA Protein Sequence
   1 MAKRLVLFAA VVIALVALTT AEGEASRQLQ CEHELQESSL EACRQVVDQQ LAGRLPWSTG
  61 LQMRCCQQLR DVSAKCRSVA VSQVARQYEQ TVVPPKGGSF YPGETTPLQQ LQQGIFWGTS
 121 SQTVQGYYPS VTSPRQGSYY PGQASPQQPG QGQQPGKWQE PGQGQQWYYP TSLQQPGQGQ
 181 QIGKGKQGYY PTSLQQPGQG QQIGQGQQGY YPTSPQHTGQ RQQPVQGQQI GQGQQPEQGQ
 241 QPGQWQQGYY PTSPQQLGQG QQPGWQQSG QGQQGHYPTS LQQPGQGQQG HYLASQQQPA
 301 QGQQGHYPAS QQQPGQGQQG HYPASQQQPG QRQQGHYPAS QQQPGQGQQG HYPASQQEPG
 361 QGQQGQIPAS QQQPGQGQQG HYPASLQQPG QQGHYPTSLQ QLGQGQQIGQ PGQKQQPGQG
 421 QQTGQGQQPE QEQQPGQGQQ GYYPTSLQQP GQGQQGQGQ QGYYPTSLQQ PGQGQQGHYP
 481 ASLQQPGQGQ PGQRQQPGQG QHPEQGQQPG QGQQGYYPTS PQQPGQGQQL GQGQQGYYPT
 541 SPQQPGQGQQ PGQGQQGHCP MSPQQTGQAQ QLGQGQQIGQ VQQPGQGQQ YYPTSLQQPG
 601 QGQQSGQGQQ SGQGHQPGQG QQSGQEKQGY DSPYHVSAEQ QAASPMVAKA QQPATQLPTV
 661 CRMEGGDALS ASQ
```

FIG. 21

GENETICALLY MODIFIED BIOLOGICAL CELLS

CROSS-REFERENCE TO RELATED APPLICATIONS

This application is the national stage of International (PCT) Patent Application Serial No. PCT/US2008/061060, filed Apr. 21, 2008, which claims the benefit of the priority date of U.S. provisional application No. 60/913,043, filed Apr. 20, 2007, and U.S. provisional application No. 60/947,757, filed Jul. 3, 2007, the entire contents of each application are hereby incorporated by reference in their entirety.

This application claims the benefit of the priority date of U.S. provisional application No. 60/913,043, filed Apr. 20, 2007, and U.S. provisional application No. 60/947,757, filed Jul. 3, 2007, the entire contents of which are hereby incorporated by reference in their entirety.

FIELD OF THE INVENTION

This invention relates to the fields of microbiology and molecular biology and more particularly to altering gene expression in bacteria and other cell types to produce environmentally or therapeutically useful proteins.

BACKGROUND OF THE INVENTION

Since the late 1950s and early 1960s, molecular biologists have learned to characterize, isolate, and manipulate the molecular components of cells and organisms: DNA, RNA, and proteins. The discovery of polymerase chain reaction in the 1970s enabled biologists to amplify DNA to quantities that could be manipulated. The isolation of restriction endonucleases in the 1970s significantly advanced molecular biology, allowing for the production of recombinant nucleic acids and proteins.

One of the most basic techniques of molecular biology used to study protein function is expression cloning, which was developed in large part using *E. coli*. In this technique, DNA coding for a protein of interest is cloned (using PCR and/or restriction enzymes) into a plasmid or other expression vector. This plasmid may have replication elements so that it is maintained in a host cell (e.g., an *E. coli* cell), special promoter elements to drive production of the protein of interest, and may also have antibiotic resistance markers to help follow the plasmid.

Expression cloning has allowed for the recombinant production of proteins, which avoids many of the difficulties and hazards of protein purification from natural sources. For example, the recombinant production of human proteins eliminates workers' exposure to human fluid and tissues, avoiding potential exposure to infectious agents such as viruses. In the case of many environmentally, industrially, and therapeutically useful proteins, recombinant manufacturing is frequently the only practical method for producing the amounts of protein required for use or sale. However, the requirements and needs for large scale recombinant production of proteins are distinct from those of small scale production as would occur, for example, in a research laboratory.

SUMMARY OF THE INVENTION

The present invention is based, in part, on our discovery of a way to configure expression cassettes so that the expression of a selectable marker protein, which is critical for the growth or survival of a cell, also results in the expression of a protein of interest in a biological cell. Accordingly, in one aspect, the invention features a genetically modified cell (e.g., a bacterial cell) that includes a chromosomally integrated or cytoplasmic expression cassette that includes a first nucleic acid sequence encoding a protein of interest and a second nucleic acid sequence encoding a selectable marker protein. The regulatory sequence (e.g., the sequence encoding a functional promoter) that drives expression of the required selectable marker protein also drives expression of the protein of interest. For that reason, we may refer to their expression as being "linked" or "functionally coupled."

In some embodiments, a selectable marker is defined as an amino acid sequence that, in a population of cells derived from a parent cell to which a nucleic acid encoding the selectable marker was first introduced, was capable of acting as a selectable marker in the parent cell given the genomic constitution of the parent cell at the time the nucleic acid encoding the selectable marker was introduced into the parent cell.

In some embodiments, the protein of interest is not a purification or epitope tag.

The genetically modified cell can be a bacterial cell (e.g., a cyanobacterium). For example, the genetically modified bacterial cell can belong to one of the following species: *Anabaena* species (sp.), *Anabaenopsis* sp., *Aphanizomenon* sp., *Arthrospira* sp., *Calothrix* sp., *Chamaesiphon* sp., *Chlorogloeopsis* sp., *Chroococcidiopsis* sp., *Chroococcus* sp., *Cyanothece* sp., *Cylindrospermum* sp., *Dactylococcopsis* sp., *Dermocarpella* sp., *Fischerella* sp., *Geitlerinema* sp., *Gloeobacter* sp., *Gloeocapsa* sp., *Gloeothece* sp., *Leptolyngbya* sp., *Lyngbya* sp., *Microchaete* sp., *Microcoleus* sp., *Microcystis* sp., *Myxosarcina* sp., *Nodularia* sp., *Nostoc* sp., *Oscillatoria* sp., *Pleurocapsa* sp., *Pseudanabaena* sp., *Scytonema* sp., *Spirulina* sp., *Stanieria* sp., *Symploca* sp., *Synechococcus* sp., *Synechocystis* sp., *Tolypothrix* sp., or *Xenococcus* sp. In some embodiments, the genetically modified bacterial cell can belong to one of the following species: *Calothrix* sp., *Geitlerinema* sp., *Myxosarcina* sp., *Pleurocapsa* sp., or *Stanieria* sp.

The protein of interest that is expressed by the genetically modified bacterial cell can be a bacterial, plant, or mammalian protein and the nucleic acid sequence from which a protein of interest is expressed can be codon optimized so that it is optimally expressed in the genetically modified bacterial cell. The protein of interest can be a metal-binding protein. For example, the metal-binding protein can be a metallothionein, a transcription factor, or an enzyme. The protein of interest can be an enzyme. For example, the enzyme can be a protease, an oxidase, a phytase, a chitinase, an invertase, a lipase, a cellulase, a xylenase, a kinase, a phosphatase, an enzyme within a biosynthetic pathway that results in the production of an oil, an enzyme active in the synthesis of fatty acids 10-16 carbons in length, an enzyme that accelerates fructose metabolism, an enzyme that accelerates glycerol metabolism (e.g., glycerol kinase or glycerol 3-phosphate dehydrogenase), or an enzyme that converts lactic acid to pyruvate (e.g., lactate dehydrogenase M4). The protein of interest can be an enzyme active in the synthesis of fatty acids 10-16 carbons in length, for example, pyruvate dehydrogenase, dihydrolipoyl dehydrogenase, dihydrolipoyllysine-residue acetyltransferase, acteyl-CoA carboxylase, malonyl-CoA:ACP transacylase, and fatty acid synthase.

The protein of interest can be a protein that accelerates fructose metabolism or a protein that increases fructose transport into a cell, for example, hepatic fructokinase, aldolase B, glyceraldehyde kinase, or a protein belonging to the ATP-binding cassette transporter (ABC-transporter) family and that transports fructose (e.g., phosphoenolpyruvate-protein phosphotransferase, HPr protein or protein-Nπ-phosphohistidine-sugar phosphotransferase (fructose-specific)).

The protein of interest can be an immunogen, a soluble protein, an anti-toxin, a plant protein (e.g., zein), a mammalian protein, a hormone, a transcription factor, a growth factor, an anticoagulant, a lysosomal protein, an enzyme substrate, a receptor or a subunit thereof, a heavy chain of an immunoglobulin, a light chain of an immunoglobulin, or a single chain antibody. In certain embodiments, the protein of interest is an immunogen which is part of a fusion protein. In some embodiments, the protein of interest is a mammalian protein (e.g., a mammalian hormone, a mammalian transcription factor, a mammalian growth factor, a mammalian anticoagulant, a mammalian lysosomal protein, a mammalian enzyme substrate, a mammalian receptor or a subunit thereof, a mammalian heavy chain of an immunoglobulin, a mammalian light chain of an immunoglobulin, or a mammalian single chain antibody).

In some embodiments, the genetically modified bacterial cell express a positive selectable marker protein, for example, an enzyme within a biosynthetic pathway that produces an essential nutrient or an enzyme within a biosynthetic pathway that produces a vitamin. In some embodiments, the positive selectable marker is an enzyme within a biosynthetic pathway that produces any one of the following essential nutrients: ascorbic acid (vitamin C), biotin (vitamin B7), choline, folic acid (vitamin B9), inositol, nicotinic acid/niacin (vitamin B3), para-aminobenzoic acid (PABA), pantothenic acid (vitamin B5), pyridoxine (vitamin B6), riboflavin (vitamin B2), thiamine (vitamin B1), thymidine retinoid (vitamin A), tocopherol (vitamin E), naphthoquinon (vitamin K), ergocalciferol (vitamin D), or the pantothenic acid derivative coenzyme A. In certain embodiments, the bacterial cell expresses an enzyme within a biosynthetic pathway that produces vitamin B12. The enzymes found at the following genomic loci, for example, can be used as positive selectable markers: cobA, cobI, cobG, cobJ, cobM, cobF, cobK, cobL, cobH, cobB, cobN, cysG, cbiK, cbiX, cbiL, cbiH, cbiF, cbiD, cbiJ, cbiE, cbiT, cbiC, cbiA, cob(II) a,c-diamide reductase, cobO, cobP, BtuR, cobQ, cbiP, cobC, codD, cbiB, cobU, cobV and cobS.

The protein of interest may include a purification tag such as a histidine tag, a calmodulin binding peptide (CBP) tag, a immunoglobulin (Ig) tag, a maltose-binding protein (MBP) tag, a Chitin binding domain (CBD) tag or a glutathione-S-transferase (GST) tag.

In some embodiments, the genetically modified bacterial cell carries an expression cassette that includes a nucleic acid sequence encoding a purification tag that is functionally coupled to the first nucleic acid sequence. The purification tag can be a histidine tag, a calmodulin binding peptide (CBP) tag, a immunoglobulin (Ig) tag, a maltose-binding protein (MBP) tag, a Chitin binding domain (CBD) tag or a glutathione-S-transferase (GST) tag. The expression cassette may include a single promoter inserted upstream from the first nucleic acid sequence. The promoter may be naturally associated with the second nucleic acid sequence. The genetically modified bacterial cell may carry an expression cassette that includes a sequence encoding a linker between the protein of interest and the selectable marker protein and the linker may, or may not be, cleavable. In addition, the expression cassette may include a third nucleic acid sequence encoding a transcription fact and upstream from the first nucleic acid sequence, a promoter that is driven by that transcription factor.

In one aspect, this invention includes an expression cassette including a first nucleic acid sequence encoding a protein of interest and a second nucleic acid sequence encoding a selectable marker protein. In some embodiments, the expression cassette includes a single promoter inserted upstream from the first nucleic acid sequence. In some embodiments, the promoter is one that is naturally associated with the second nucleic acid sequence. The expression cassette may further include a nucleic acid sequence encoding a linker between the protein of interest and the selectable marker protein and this linker may be cleavable. The expression cassette may further include a nucleic acid sequence encoding a purification tag that is functionally coupled to the protein of interest. In some embodiments, the expression cassette includes a third nucleic acid sequence encoding a transcription factor and, upstream from the first nucleic acid sequence, a promoter that is driven by the transcription factor. In some embodiments, the expression cassette includes a first nucleic acid sequence encoding a protein of interest and a second nucleic acid sequence encoding an enzyme within a biosynthetic pathway that produces an essential nutrient. In these embodiments, the essential nutrient can be a vitamin, for example, ascorbic acid (vitamin C), biotin (vitamin B7), choline, folic acid (vitamin B9), inositol, nicotinic acid/niacin (vitamin B3), para-aminobenzoic acid (PABA), pantothenic acid (vitamin B5), pyridoxine (vitamin B6), riboflavin (vitamin B2), thiamine (vitamin B1), thymidine retinoid (vitamin A), tocopherol (vitamin E), naphthoquinon (vitamin K), ergocalciferol (vitamin D), the pantothenic acid derivative coenzyme A, or vitamin B12. In some embodiments, the expression cassette includes a nucleic acid sequence encoding a purification tag that is functionally coupled to the protein of interest. In some embodiments, the expression cassette includes a single promoter inserted upstream from a nucleic acid encoding the protein of interest. In some embodiments, the expression cassette is carried in an expression vector.

In one aspect, this features a fusion protein that includes a protein of interest and an enzyme within a biosynthetic pathway that produces an essential nutrient. The protein of interest and the enzyme are optionally linked by a cleavable or non-cleavable linker.

In one aspect, this invention features methods of genetically modifying a cyanobacterium. The method includes steps of providing a cyanobacterial cell and performing targeted replacement of a nucleic acid sequence within the cyanobacterial cell that encodes a positive selectable marker (i.e., a protein critical for cell growth or survival) with a nucleic acid sequence that encodes a negative selectable marker. The method can optionally include a further step of performing targeted replacement of the nucleic acid sequence that encodes the negative selectable marker with a nucleic acid sequence encoding (i) a protein of interest and (ii) a nucleic acid sequence encoding the positive selectable marker. The positive selectable marker can be an enzyme within a biosynthetic pathway that produces an essential nutrient or a gene critical for cell growth and survival under specified conditions. The negative selectable marker can be a protein that confers antibiotic resistance.

In one aspect, this invention features genetically modified cells (e.g., cyanobacteria) that are made by the methods described herein.

In one aspect, this invention features methods of producing a protein of interest including the steps of (a) culturing a genetically modified cyanobacterium made by the methods described herein under conditions that permit expression of a protein of interest; and (b) isolating the protein of interest from the cyanobacterium.

In one aspect, this invention includes methods of removing a metal from a metal-containing material. One or more of the methods of this invention may include steps of contacting the metal-containing material with a genetically modified cell expressing a metal-binding protein. Alternatively, the method may include steps of contacting the metal-containing material with a metal-binding protein produced by the methods described herein. These methods may be used to remove metal from soil or water. In additions, some or all of these methods may be used to remove metal-containing material from within a patient.

In one aspect, this invention includes methods of accelerating fructose metabolism. One or more of the methods of this invention may include steps of contacting a fructose-containing material with a cell expressing an enzyme that accelerates fructose metabolism or increases cellular uptake of fructose as described herein. The cell may express hepatic fructokinase, aldolase B, or glyceraldehyde kinase. The fructose-containing material can include water.

In some embodiments of this invention, the nucleic acid sequences that are contained in the expression cassettes are not immediately upstream or downstream from one another in a naturally occurring bacterial cell.

Other features and advantages of the present invention will be apparent from the following description, the drawings, and the claims.

BRIEF DESCRIPTION OF THE DRAWINGS

FIG. 1A is a schematic diagram of an expression cassette containing lac promoter and terminator elements and a nucleic acid sequence encoding a metal sequestering protein.

FIG. 1B is a schematic diagram of an expression cassette containing a single promoter element to drive transcription of an mRNA encoding a metal sequestering protein (a protein of interest) and a selectable marker protein. A single terminator element lies downstream from the selectable marker sequence.

FIG. 2A is a schematic diagram of the chromosomal region flanking a targeted enzyme, which may be examined for use as a selectable marker protein.

FIG. 2B is a schematic diagram of an expression cassette carrying a nucleic acid sequence that, when expressed, confers resistance to tetracycline (a negative selectable marker). The sequence is flanked by sequences encoding the targeted enzyme (FIG. 2A) and further by non-coding sequences that are homologous to the chromosomal sequences flanking the gene encoding the targeted enzyme.

FIG. 2C is a schematic diagram of a portion of the chromosome that results from homologous recombination between sequences flanking the targeted enzyme gene and sequences on the expression cassette shown in FIG. 2B. PCR can be used (as indicated by the overlapping arrows representing primer extension) to confirm proper insertion of the negative selectable marker. Where the targeted enzyme is within a biosynthetic pathway that produces an essential nutrient, modified cells will survive in culture media containing the essential nutrient and tetracycline but not in culture media lacking the essential nutrient. Cells that survive despite a lack of the externally supplied nutrient are discarded, as the targeted enzyme has not been knocked out effectively.

FIG. 3A is a schematic diagram of the modified chromosomal region shown in FIG. 2C.

FIG. 3B is a schematic diagram of an expression cassette encoding an engineered protein (a protein of interest) and a replacement enzyme (which can be a positive selectable marker protein) flanked by sequences that are homologous to those flanking the tetracycline resistance gene shown in FIG. 3A.

FIG. 3C is a schematic diagram of a portion of a recombinant chromosome that results from homologous recombination between the chromosomal sequences flanking the tetracycline resistance gene and sequences on the expression cassette shown in FIG. 3B. PCR can be used (as indicated by the overlapping arrows representing primer extension) to confirm proper insertion of the cassette carrying the protein of interest and the positive selectable marker (here, the replacement enzyme). Where the targeted enzyme is within a biosynthetic pathway that produces an essential nutrient, modified cells will survive in culture media lacking the essential nutrient and will express the engineered protein of interest. Cells that survive despite a lack of the externally supplied nutrient are retained, as the targeted enzyme has now been knocked in effectively.

FIG. 5 is a schema of vitamin B12 synthesis substrates/products, including corresponding enzyme names (bold), Enzyme Commission numbers and gene loci (italic) for *Synechococcus* cyanobacteria.

FIG. 6 is a Table of chemoheterotrophic cyanobacteria available as candidates for engineering.

FIG. 7 is a Table of enzymes proposed for use as described herein.

FIG. 19 is a table listing sources of CoA biosynthesis enzymes.

FIG. 20 is a representation of the nucleic acid and amino acid sequence of *Zea mays* (corn) zein NM_001112761.

FIG. 21 is a representation of the nucleic acid and amino acid sequence of the high molecular weight glutenin subunit of *Triticum aestivum* (bread wheat). EU266533.

DETAILED DESCRIPTION

Figure 4A:
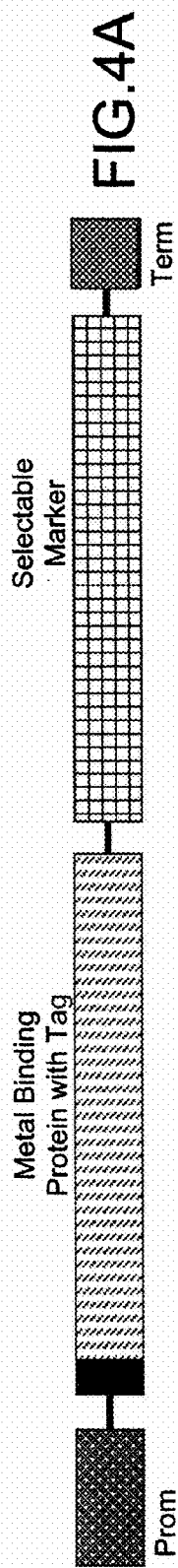
FIG. 4A is a schematic diagram of an expression cassette with a single promoter element driving transcription of an mRNA encoding a tagged metal-binding protein and a selectable marker. A single termination sequence is also shown.
Figure 4B:
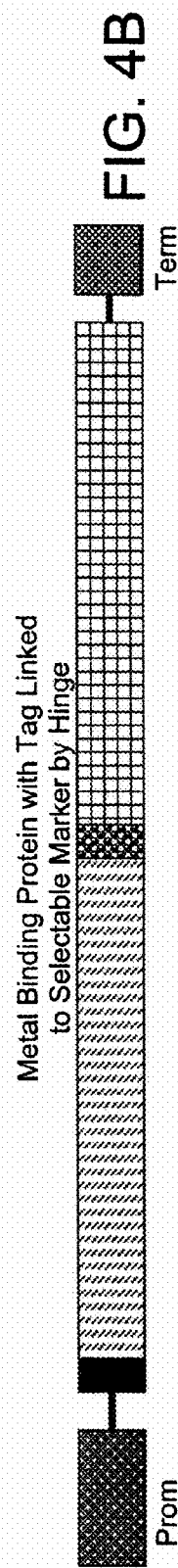
FIG. 4B is a schematic diagram of an expression cassette that is identical to the cassette shown in FIG. 4A except for the inclusion of a sequence encoding a hinge between the tagged metal sequestering protein and the selectable marker protein.
Figure 4C:
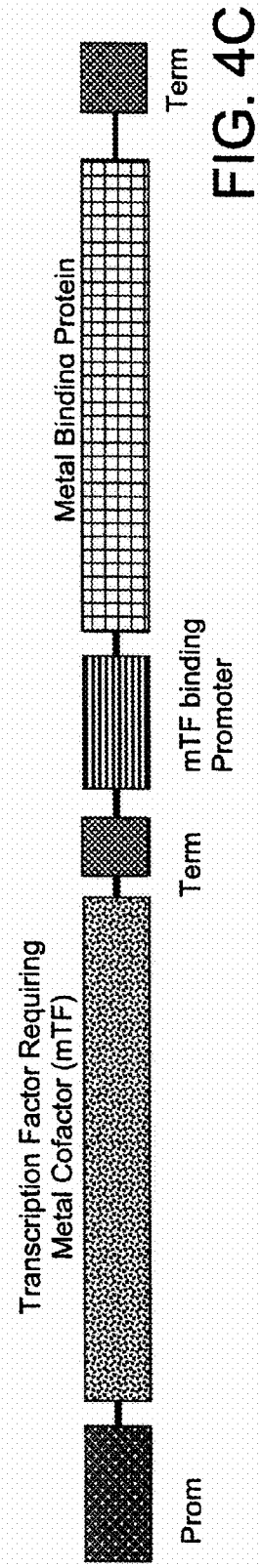
FIG. 4C is a schematic diagram of an expression cassette that contains one promoter and termination sequence to regulate the expression of a transcription factor requiring a metal cofactor (mTF) and another promoter, an mTF-binding promoter, and another terminator to regulate the expression of a selectable marker.

The present invention features, inter alia, methods of coupling the expression of a protein of interest (e.g., an environmentally, industrially, or therapeutically useful protein) to the expression of a selectable marker in a host cell (e.g., a cyanobacterium). In order to be viable (and optionally, to have a growth advantage) the host cells must express the selectable marker and in so doing, also expresses the protein of interest. We may use the term "functionally coupled" to describe this linked expression.

Methods of Making Genetically Modified Cells; Expression Cassettes for Functional Coupling (Expression Linking):

In one embodiment of the present invention, a single promoter is used to drive the transcription of DNA within an expression cassette that encodes at least one (e.g., two or three) protein of interest and at least one (e.g., two or three) selectable marker protein. The DNA encoding the selectable marker protein can be positioned downstream from the DNA encoding the protein of interest, so the sequence encoding the protein of interest lies between the sequence encoding the selectable marker and its promoter. A single polycistronic mRNA encoding both the protein of interest and the selectable marker protein is then produced and translated to generate the two encoded proteins. Thus, transcription of mRNA encoding the protein of interest and transcription of the selectable marker, while linked, results in the production of two separate proteins. Where a termination signal is missing from the 3' end of the "first" sequence (i.e., the sequence more toward the 5' end of the mRNA (e.g., an mRNA encoding the protein of interest), and that mRNA is contiguous with the mRNA encoding the selectable marker protein, the translated product is a fusion protein; the protein of interest is fused by a peptide bond to the selectable marker protein. A hinge or linker may also be included so that the resulting protein of interest and the selectable marker protein, while still fused, are separated by the hinge or linker, which may include a cleavage site. The promoter can be the promoter naturally associated with the selectable marker protein.

In other embodiments, expression is linked because transcription of the mRNA encoding the protein of interest and transcription of the mRNA encoding the selectable marker are driven by two copies of the same promoter. Although two mRNA transcripts are produced (one encoding the protein of interest and another encoding a selectable marker), transcription of one mRNA is coupled to transcription of the other since transcription of both mRNAs is dependent on the same promoter (the two copies of the promoter are expected to be active at the same time).

In some embodiments, expression of the protein of interest is linked to transcription of the selectable marker in that the protein of interest promotes transcription of the selectable marker. In certain embodiments, the protein of interest is a transcription factor that binds to the promoter associated with the selectable marker and drives selectable marker expression. Since expression of the protein of interest and expression of the selectable marker are coupled (according to the methods of this invention), this creates a positive feedback loop that maximizes expression of the protein of interest. In certain embodiments, the protein of interest is a transcription factor, which is also a metal binding protein.

In any of the embodiments described above, the protein of interest can be fused, directly or indirectly, to a tag (e.g., a sequence that facilitates identification or purification).

The protein of interest and the selectable marker protein are described further below. Generally, either of these proteins can exhibit a certain degree of identity (including 100%, or nearly 100% (e.g., at least 98% or at least 99%) identity) to a corresponding wild type protein. While we tend to use the term "protein," we may use the terms "protein," "polypeptide," or "peptide" to refer to any chain of amino acid residues, regardless of length, specific content (e.g., mutations or the inclusion of non-naturally occurring amino acid residues), or other features (e.g., the inclusion of sugars, which may be added after translation).

While we discuss here the extent or degree of identity of one polypeptide to another, the variability in sequence extends to the extent or degree of variation in the nucleic acid molecules that encode the proteins in question and that are useful in carrying out the methods described herein. For example, any of the nucleic acid sequences within an expression cassette can exhibit a certain degree of identity to a corresponding wild type nucleic acid sequence.

Proteins or nucleic acid sequences that vary from wild type can be used in the present methods so long as they retain the ability to function sufficiently well. We may refer to these variants as "biologically active variants." The protein variants may differ from the corresponding wild type protein sequences by virtue of having one or more substitutions, additions or deletions of one or more amino acid residues. Similarly, biologically active variants of the nucleic acid sequences included in the present expression cassettes can give rise to conservative or non-conservative substitutions or can be "silent" variants by virtue of the "wobble" allowed in the third position.

Where amino acid substitutions are made, they may be conservative or non-conservative substitutions. Where a conservative amino acid substitution is made, the substitution can be of one amino acid residue for another in any of the following groups: arginine, histidine, and lysine; aspartic acid and glutamic acid; alanine, leucine, isoleucine and valine; and phenylalanine, tryptophan and tyrosine. Non-naturally occurring amino acid residues of like kind may also be substituted. For example, a negatively charged non-naturally occurring amino acid residue may be substituted for a negatively charged naturally occurring amino acid residue; a hydrophobic aromatic non-naturally occurring amino acid residue may be substituted for a hydrophobic aromatic naturally occurring amino acid residue; and so forth.

The degree of identity can vary. For example, useful protein or nucleic acid sequence can be at least or about 50%, 65%, 75%, 80%, 85%, 90%, 95%, 96%, 97%, 98%, or 99% identical to a corresponding naturally occurring amino acid or nucleic acid sequence, respectively.

We will now further describe the proteins of interest, the selectable marker proteins, the hinge or linker, and the tag.

Proteins of Interest:

Because of the fundamental ability of the present expression linked system to generally support protein production, the invention encompasses expression of virtually any protein. The protein can be one that is environmentally, industrially, or therapeutically useful, and it may be one whose sequence is either artificially designed (i.e., purposefully made as a non-naturally occurring protein) or found in nature. For example, the protein can have a sequence naturally found in a bacterial, fungal, viral, plant, mammalian, or avian genome or within the genome of a fish or bivalve. The mammalian protein can be, for example, that of a human, a rodent, a pig, a sheep, a horse, a goat, a cow, a dog, a cat, or a non-human primate.

With respect to function, the protein of interest can be a metal-binding protein, an enzyme, an immunogen, a toxin or antitoxin, a prolamine such as zein, a hormone, a transcription factor, a growth factor (including an interleukin or cytokine), an anticoagulant, a lysosomal protein, an enzyme substrate, a receptor or a subunit thereof, a heavy chain of an immunoglobulin, a light chain of an immunoglobulin, a single chain antibody, or a structural protein such as fibronectin or collagen. As noted above, the protein can be a biologically active variant of a naturally occurring protein. Where a naturally occurring protein is useful in a given process (e.g., in an industrial process such as ethanol biosynthesis or fatty acid biosynthesis), a biologically active variant of that protein is useful as well.

The proteins of interest can be expressed singly or in conjunction, from the same or different expression cassettes, such that, in some instances, expression results in the creation (or restoration of) a biosynthetic pathway for carbohydrates, lipids, glycoproteins or other biochemicals or essential nutrients.

While we have set out various types of proteins from various sources for various uses, it is to be understood that any given protein may be appropriately described in more than one way. For example, a given protein may be useful in both environmental processes and therapeutic settings (by, for example, sequestering metal from a water supply or from within a patient's body).

Metal-Binding Proteins:

Many metal-binding proteins are known in the art and can be expressed by the present methods. Examples of known metal-binding proteins include, but are not limited to, transcription factors, metallothioneins, transferrins, and globins. These and other metal binding proteins are described, for example, in U.S. Patent Publication Nos. 2007/0281333, 2007/0117968, 2003/0088083, and 2003/0104524.

Enzymes:

The methods and cells described herein may be used to express enzymes, which may be environmentally, industrially, or therapeutically useful. The enzymes include, but are not limited to, those within the following classes: an oxidase, a phytase, a chitinase, an invertase, a lipase, a cellulase, a xylenase, a kinase, a phosphatase, or an enzyme within a biosynthetic pathway that results in the production or degradation of an oil.

Useful enzyme can be further characterized (in a non-limiting fashion) as (a) an enzyme active in the synthesis of fatty acids 10-16 carbons in length; (b) an enzyme that accelerates fructose metabolism; (c) an enzyme that accelerates glycerol metabolism; or (d) an enzyme that converts lactic acid to pyruvate.

Examples of enzymes that are useful in biosynthetic pathways that result in the production of a fatty acid (10-16 carbons in length) and essential amino acids include, but are not limited to, pyruvate dehydrogenase, dihydrolipoyl dehydrogenase, dihydrolipoyllysine-residue acetyltransferase, acetyl-CoA carboxylase, malonyl-CoA:ACP transacylase, fatty acid synthase, enzymes that accelerate fructose metabolism (for example, hepatic fructokinase, aldolase B, or glyceraldehyde kinase), enzymes that accelerate glycerol metabolism (for example, glycerol kinase or glycerol 3-phosphate dehydrogenase), or enzymes that convert lactic acid to pyruvate (for example, lactate dehydrogenase M4).

Immunogens:

The present compositions and methods can be used to produce immunogens for, for example, inclusion in vaccine preparations. The immunogen may be a protein or peptide of any sequence or size so long as it elicits an immune response. Suitable immunogenic peptides can consisting of or include an amino acid sequence of at least seven amino acid residues (e.g., eight, nine, or 10 amino acid residues). The immunogens may be useful for preparing antibodies against a protein or eliciting an immune response in a mammal (e.g., livestock, domestic pets, and humans).

Hydrophobicity plot analysis can be used, if desired, to identify immunogenic sequences and to help predict immunogenicity. The immunogenic peptides may contain all or part of a hydrophilic or hydrophobic region of a protein from which they are derived and may include one or more extracellular regions of a protein.

Where an immune response is elicited or enhanced, the response can include an antibody-mediated immune response and/or a cell-mediated immune response. For example, cytotoxic T cells (CTLs) can be generated, resulting in a cytolytic immune response. Accordingly, the immunogen can include the sequence of one or more B cell and/or T cell epitopes.

Related to the production of immunogens, proteins useful as adjuvants are also proteins of interest that can be made using the present compositions and methods (e.g., a cytokine such as IL-1 or IL-2, or a non-toxic mutant of a toxic protein (e.g., cholera toxin, pertussis toxin, and/or *E. coli* heat labile toxin)).

Examples of peptides that may serve as immunogens include but are not limited to viral proteins, bacterial proteins, and fungal proteins, any of which may be included in a fusion protein with a heterologous protein (e.g., all or a part of a heat shock protein).

Toxins and Antitoxins:

Engineered host cells (e.g., cyanobacteria) can be used to rapidly and inexpensively produce a wide range of toxins and anti-toxins. For example, the toxins produced by the methods described herein can be a neurotoxin (e.g., botulinum neurotoxin, which is produced by the bacterium *Clostridium botulinum* and frequently used to treat wrinkles, muscle spasms and migraine headaches).

The protein of interest can also be an anti-toxin, such as an enzyme that destroys a toxin or a ligand that irreversibly binds the toxin, rendering it inactive. The target toxin can also be a botulinum neurotoxin, which is highly dangerous. Current treatments are based on horse antiserums or purified horse antibody fragments. These antibodies, or other antigen binding polypeptides such as single chain FVs (scFV) can be produced by the methods and cells described herein.

The basic antitoxin production process could involve growing engineered cells (e.g., cyanobacteria) where they are needed. Cyanobacteria grow very slowly when stored in low light and minimal conditions and then become active when given proper nutrients and higher light. This would allow small stocks to be transported for long distances and then put into large scale production and use where and when needed.

Prolamines:

Gluten-derived proteins are found in high concentrations in various grains, such as corn, wheat, barley, rice and sorghum, as well as in other plants and animal sources, and can be expressed in the present expression linked system (e.g., in cyanobacteria). More specifically, cells can be modified as described herein to express a prolamine such as zein, hordein, gliadin or kafirin, a glutenin or glutelin. Once generated, the gluten-derived proteins can be used in a number of ways, including use in film-forming colloidal dispersions as described in U.S. Pat. No. 5,736,178.

Zein is the major storage protein in corn kernels. Zein's water-insoluble characteristics make it useful in a wide variety of products including biodegradable packaging and the like (e.g., coatings for paper cups and bottle cap linings) and pharmaceutical coatings. Zein can also be used in the textile fibers market and is classified as GRAS (Generally Recognized As Safe) the U.S. Food and Drug Administration.

A particular sequence, that encoding Zea mays (corn) zein, useful in the present expression cassettes has been assigned the accession number NM_001112761 and is shown in FIG. 20.

Wheat gluten is composed of the proteins gliadin and glutenin, which are proteins of interest, along with carbohydrates. Glutenin contains a combination of high-molecular weight and low-molecular weight subunits, with the type and concentration of the high-molecular weight subunits determining how elastic the protein will be. Gliadin has multiple sub-types and specific sub-types are critical in triggering the detrimental effects often seen in gluten-dependent sensitivities.

A particular sequence, that encoding the high molecular weight glutenin subunit of Triticum aestivum (bread wheat), has been assigned the accession number EU266533 and is shown in FIG. 21.

Hormones:

Any of the protein or peptide hormones (e.g., insulin, a growth hormone or a thyroid hormone can be expressed as a protein of interest using the compositions and methods described herein.

Transcription Factors:

Transcription factors bind to transcription regulatory sequences and activate (or inhibit) the transcription of a gene with which the regulatory sequence is associated and some transcription factors are known to bind metals such as zinc. The methods and cells described herein are useful for expressing transcription factors. Examples of transcription factors that may be expressed by the methods described herein include transcription factors that act as tumor suppressors.

Growth Factors:

Growth factors are proteins that stimulate the growth and proliferation of cells. Methods of assaying growth factor are known in the art. For example, a candidate growth factor can be assayed for its ability to induce proliferation in a cultured cell population (for example, lymphocytes or fibroblasts). A growth factor can be a cytokine or interleukin, and examples of growth factors that are known in the art and can be produced using the compositions and methods described herein are: a transforming growth factor-β1 (TGF β1), a transforming growth factor β2 (TGF β2), a basic fibroblast growth factor (bFGF), a fibroblast growth factor (e.g., FGF 7), a platelet-derived growth factor (PDGF-BB), a vascular endothelial growth factor A (VEGF-A), a nerve growth factor (NGF), and a glial growth factor (a GGF).

Anticoagulants:

Anticoagulants are proteins that prevent the coagulation of blood and are useful in treating thrombotic disorders, including, but not limited to, deep vein thrombosis, pulmonary embolism, myocardial infarctions and strokes. For example, protein inhibitors of the enzyme thrombin (e.g., antibodies, fragments, or antibody variants) may be produced by the compositions and methods described herein. Thrombin is an enzyme that is known in the art to promote blood clotting.

Lysosomal Proteins:

Recombinant lysosomal proteins can also be produced according to the invention and find use in enzyme replacement therapeutic procedures. A patient having a genetic or other deficiency resulting in an insufficiency of functional lysosomal enzyme can be treated by administering exogenous enzyme to the patient. Patients in need of such treatment can be identified from symptoms (e.g., Hurler's syndrome symptoms include Dwarfism, corneal clouding, hepatosplenomegaly, valvular lesions, coronary artery lesions, skeletal deformities, joint stiffness and progressive mental retardation). Alternatively, or additionally, patients can be diagnosed from biochemical analysis of a tissue sample to reveal excessive accumulation of a characteristic metabolite processed by a particular lysosomal enzyme or by enzyme assay using an artificial or natural substrate to reveal deficiency of a particular lysosomal enzyme activity.

There are over thirty lysosomal diseases, each resulting from a deficiency of a particular lysosomal protein, usually as a result of genetic mutation (see, e.g., Cotran et al., Robbins Pathologic Basis of Disease (4th ed. 1989) and these proteins are among the proteins of interest that can be made using the present compositions and methods. Specific examples of lysosomal proteins are described in U.S. Pat. No. 6,118,045 and include, but are not limited to: α-glucosidase, α-L-iduronidase, iduronate-sulfate sulfatase, hexosaminidase A and B, ganglioside activator protein, arylsulfatase A and B, iduronate sulfatase, heparan N-sulfatase, galactoceramidase, α-galactosylceramidase A, sphingomyelinase, α-fucosidase, α-mannosidase, aspartylglycosamine amide hydrolase, acid lipase, N-acetyl-α-D-glucosamine-6-sulphate sulfatase, α- and β-galactosidase, β-glucuronidase, β-mannosidase, ceramidase, galactocerebrosidase, α-N-acetylgalactosaminidase, and protective protein and others. Allelic, cognate and induced variants of any of the known lysosomal protein gene sequences are also included.

Enzyme Substrates:

An enzyme substrate is any protein that is acted upon by an enzyme, and these proteins can be made using the compositions and methods described herein.

Receptors:

Receptor binding to ligand induces changes in cellular signaling that effect cell proliferation, cell motility, cell viability, cellular morphology, and transcription. If not regulated appropriately, these cellular processes can be induce disease states, for example, hyperproliferative disorders, cancer, and autoimmune disease. Receptors can be classified as membrane bound receptors or nuclear hormone receptors, and either type, from any species, can be produced using the compositions and methods described herein. Soluble receptor isoforms of membrane bound receptors can be used, for example, to inhibit ligand binding to the membrane bound receptor.

Antibodies:

Antibody proteins can be expressed using the methods and cells described herein, including chimeric, human, and humanized antibodies. A chimeric antibody is an antibody comprising the antibody heavy chain and light chain variable regions of a nonhuman mammal such as a mouse, and the antibody heavy chain and light chain constant regions of a human. A humanized antibody, which may also be called a reshaped human antibody, is obtained by transplanting a complementarity determining region (CDR) of an antibody of a nonhuman mammal such as a mouse, into the CDR of a human antibody. As eukaryotic host cells, animal cells, plant cells, and fungal cells may be used. Known animal cells include: (1) mammalian cells such as CHO, COS, myeloma, baby hamster kidney (BHK), HeLa, and Vero cells; (2) amphibian cells such as *Xenopus oocytes*; or (3) insect cells such as sf9, sf21, and Tn5. Known plant cells include cells derived from the *Nicotiana* genus such as *Nicotiana tabacum*, which can be callus cultured. Known fungal cells include yeasts such as the *Saccharomyces* genus, for example *Saccharomyces cerevisiae*, and filamentous fungi such as the *Aspergillus* genus, for example *Aspergillus niger*. Prokaryotic cells can also be used in production systems that utilize bacterial cells. Known bacterial cells include *E. coli* and *Bacillus subtilis*. These cells can be used as host cells for the present expression cassettes and, in certain embodiments, the host cells are cyanobacterial cells. By transferring the antibody genes of interest into these cells using transformation, for example, and then culturing the transformed cells in vitro, the antibodies can be obtained.

Furthermore, the antibody may be an antibody fragment or a modified antibody thereof that is expressed recombinantly using the methods and cells of this invention. For example, the antibody fragment may be Fab, F(ab')2, Fv, single chain Fv (scFv) in which Fv from H or L chains are ligated by an appropriate linker, or diabody.

Structural Proteins:

Structural proteins are those proteins having, as their primary purpose, the production and/or maintenance of the essential structure of the cell. Examples of the structural proteins that can be produced using the present compositions and methods include, but are not limited to, actin, catenin, claudin, coilin, collagen, elastin, fibrillin, lamin, sclerotin, spongin, type-I collagen, type-II collagen, type-III collagen, viral structural proteins, keratins, silks, and insect fibers.

The Selectable Marker:

Currently, selectable markers typically used in expression cloning in bacteria are genes encoding enzymes or protein pumps that allow bacteria to survive in the presence of a selecting antibiotic. This system is problematic, particularly for environmental or industrial applications, because the pressure on the cells to maintain the desired genes can only occur if the cells are grown in high concentrations of antibiotics, and the genes that confer antibiotic resistance can jump from industrial organisms into pathogenic bacteria. The more often antibiotics and antibiotic resistant selection systems are used in industrial processes, the greater the chance for pathogenic bacteria to become antibiotic resistant.

Generally, when a critical protein that allows cellular selection is encoded as part of an engineered DNA construct, it is described as a selectable marker. After transfection or transformation, expression of the selectable marker allows a researcher to either positively or negatively select for cells that can survive in specific conditions. Selectable markers may be expressed with another gene product by, for example, placing sequences that encode them on an expression vector with each coding region being flanked by its own promoter and polyadenylation regions. The two gene products can also be encoded by independent DNA constructs, each having its own promoter and polyadenylation sequences. The DNA product encoding the selectable marker is introduced into the target cell at the same time as a DNA for the production of a desired protein. As the two separate DNA products tend to become incorporated into the cells together, the cells that survive selection by acquiring the selection marker DNA are likely to also have the second DNA construct encoding the desired protein and function. These systems differ from the present system, where the regulatory sequences (e.g., the promoter) used to drive expression of the selectable marker protein also drives expression of the protein of interest; here expression of the protein of interest is actively linked to expression of the selectable marker, which the cell must make to ensure its survival.

Expression of a gene that confers antibiotic resistance is an example of a negative selectable marker. In negative selection, cells that do not express the negative selectable marker are selected against; negative selectable markers break down or otherwise neutralize a poison. Examples of negative selectable markers that are used with bacterial host cells such as *E. coli*, for example, include markers that confer resistance against antibiotics such as tetracycline, ampicillin, and kanamycin. For example, the operational DNA construct for β-lactamase is frequently referred to as the "amp resistance gene," as it allows transformed bacteria to grow in solutions containing ampicillin.

In positive selection, cells that express the selectable marker are selected for (i.e., by virtue of survival); a positive selectable marker overcomes an environmental deficiency. Examples of positive selectable markers that can be used when the host cell is *S. cerevisiae*, for example, include URA3 and LYS2. Examples of positive selectable markers that can be used when the host cell is a cyanobacterium, for example, include enzymes and components of the vitamin B12 pathway. Examples of positive selectable markers that can be used in plant and mammalian cells include the HRPT gene, which acts as a positive selectable marker when cells expressing the marker are grown in HAT media. The HRPT DNA construct allows for positive selection by allowing nucleotides to be produced through the thymidine kinase and hypoxanthine guanine phosphoribosyl transferase pathways when the phosphoribosyl pyrophosphate pathway is blocked.

While positive or negative selection markers can be used in the present expression cassettes (including the positive and negative selection markers described above), we have also discovered new positive selection systems (and methods for identifying positive selectable markers) that can be used for RNA or protein expression in essentially any host cell, including cyanobacteria.

The basis of the present positive selection system is a mutant host cell (e.g., a strain of cyanobacteria) that is not viable under growth conditions lacking one or more essential nutrients. These cells are mutant in that, prior to the insertion of an expression cassette, they fail to express a positive selectable marker and must receive the essential nutrient from an external source in order to survive. For example, the invention features mutant strains of cyanobacteria that lack one or more of the enzymes or components of a metabolic pathway (e.g., a biosynthetic pathway) that produces the essential nutrient. When an expression cassette is introduced into such a mutant strain of cyanobacteria and expressed, one restores the function of the metabolic pathway that was defective in that host cell, allowing the cell to be grown in media lacking the essential nutrient. Only those mutant cells that subsequently include an expression cassette from which a positive selection marker protein is expressed can survive on media that does not provide the essential nutrient. As noted above, due to the active linkage achieved by placing the sequence expressing the protein of interest under the control of the promoter driving the selectable marker protein, the protein of interest is expressed together with the selectable marker.

Examples of essential nutrients produced by biosynthesis pathways include but are not limited to, cofactors, vitamins, and amino acids (e.g., biotin, choline, folic acid, inositol, nicotinic acid, PABA, panthothenic acid, pyridoxine, riboflavin, thiamine, thymidine, alanine, arginine, aspartic acid, cysteine, glutamic acid, glycine, histidine, isoleucine, leucine, lysine, methionine, phenylalanine, praline, serine, threonine, tryptophan, tyrosine, or valine). Accordingly, enzymes or other proteins that are required The metabolic pathway can be a catabolic pathway that produces an essential nutrient. For example, bacteria that can not catabolize lactose into glucose cannot grow and are not viable in an environment in which the only available carbohydrate is lactose. Thus, any nucleic acid that, when introduced into and expressed in a mutant strain that is defective in lactose catabolism, restores the ability of the strain to catabolize lactose can be used as a selectable marker.

The mutant host cells (e.g., a strain of cyanobacteria) can be those having a naturally occurring mutation or a mutation produced by recombinant methods. For example, some cyanobacteria strains have been isolated that are unable to make any cobalamine (vitamin B12) and will only survive if it is provided in the growth media (Van Baalen, *Bot. Mar.* 4:129-139, 1962). These are described as having an obligate vitamin B12 requirement. Other strains can produce some cobalamine but not at a sufficient level for rapid growth. These strains are described as vitamin B12 stimulatory. Both obligate vitamin B12 and vitamin B12 stimulatory strains can be used in the methods described herein, and examples of these naturally occurring mutant strains (available from the Institut Pasteur Culture Collection of Cyanobacteria) are provided in Table 1.

Mutant strains of host cells, including cyanobacteria, can be generated by methods known in the art. For example, one can obtain a mutant strain by exposing a host cell (e.g., a cyanobacterial cell) to a known mutagen (e.g., chemical mutagens such as ethylmethane sulfate, electromagnetic radiation such as X-rays, or DNA sequences that come to reside in a coding sequence or regulatory sequence). One can then conduct a genetic screen for mutations that specifically affect metabolic pathways (Dolganov and Grossman, *J. Bact.* 175:7644-7651, 1993; Matsuoka et al., *Microbiology* 147: 2077-2087, 2001).

A cell (e.g., a mutant strain of cyanobacteria) may also be made by sequence-specific recombinant methods that are known in the art, and recombinant knock out strains lacking, for example, a positive selectable marker, are within the scope of the present invention. These knock out strains may be mutated in any gene or genomic region that affects the function of a metabolic pathway that produces an essential nutrient or amino acid. For example, the knock out strain can have a deletion of some or all of a gene encoding an enzyme or other component of a metabolic pathway (e.g., a biosynthesis pathway resulting in an essential nutrient). Where the deletion is a partial deletion, it will be significant enough to result in the production of an essentially non-functional gene prod-

TABLE 1

Obligate Vitamin B12 and Vitamin B12 Stimulatory Strains

| Obligate Vitamin B12 | | Vitamin B12 Stimulatory | | Amino Acid Deficient | | Vitamin and Amino Acid Deficient | |
|---|---|---|---|---|---|---|---|
| Name | Category | Name | Category | Name | Category | Name | Category |
| PCC 7007 | *Gloeocapsa* | PCC 6906 | *Synechocystis* | PCC 8907 | *Geitlerinema* | PCC 7924 | *Leptolyngbya* |
| PCC 7002 | *Synechococcus* | PCC 7105 | *Geitlerinema* | PCC 9207 | *Leptolyngbya* | PCC 7925 | *Leptolyngbya* |
| PCC 7003 | *Synechococcus* | PCC 7302 | *Stanieria* | PCC 9221 | *Leptolyngbya* | | |
| PCC 7301 | *Stanieria* | PCC 73109 | *Synechococcus* | PCC 9222 | *Geitlerinema* | | |
| PCC 7317 | *Pleurocapsa* | PCC 8938 | *Synechocystis* | | | | |
| PCC 7375 | *Leptolyngbya* | PCC 8939 | *Synechococcus* | | | | |
| PCC 7376 | *Leptolyngbya* | PCC 8966 | *Synechococcus* | | | | |
| PCC 7818 | *Leptolyngbya* | PCC 8990 | *Synechocystis* | | | | |
| PCC 8103 | *Leptolyngbya* | | | | | | |
| PCC 8104 | *Leptolyngbya* | | | | | | |

As noted above, proteins involved in the synthesis of essential amino acids can also be used as positive selectable markers. Some cyanobacteria strains have been isolated that are unable to produce a full complement of amino acids. These strains require the addition of casamino acids to their media to provide the amino acids they are not able to synthesize. Accordingly, expression cassettes from which those synthetic proteins are produced, together with a protein of interest, are within the scope of the present invention and can be used in the present methods to generate proteins of interest (i.e., expression of a protein in a synthetic pathway that results in the production of an essential amino acid can be expression linked or functionally coupled as a selectable marker to expression of a protein of interest).

Some strains of cyanobacteria are unable to produce both certain necessary vitamins and amino acids. For these strains, more than one positive selectable marker may be used to restore viability, and the expression cassettes of the present invention include those that contain sequences that encode and drive the expression of more than one selectable marker.

uct. The mutation (e.g., the nucleic acid deletion) can also "knock out" a genomic region that regulates the expression of the selectable marker (e.g., an enzyme or other component of a metabolic pathway). For example, the mutation may remove transcriptional or translational regulatory regions.

The mutation(s) affecting the metabolic pathways may be of any nature (e.g., the mutation may be or may include an addition, deletion, or substitution of a nucleic acid sequence in the coding or regulatory regions of the genome).

Examples of genes that may be mutated in naturally occurring mutant strains or in engineered mutants include, but are not limited to, those described in Tables 2-5 (Tables 2-4 exemplifying selectable markers in the production of essential vitamins and Table 5 exemplifying selectable markers in the production of the essential amino acid leucine). Subsequent "knock in" of sequences that encode the "knocked out" selectable markers (or biologically active variants thereof) are then expressed, with the regulatory regions driving expression of the selectable marker arranged to drive expression of a protein of interest as well. In that way, expression of the two proteins is functionally coupled; their expression is linked.

TABLE 2

Synthesis of Thiamine (Vitamin B1)

| Substrate/Product | Enzyme | Gene | E.C. |
|---|---|---|---|
| Purine metabolism | | | |
| 1-(5'-Phosphoribosyl)-5-amino-imidazole (AIR) | THIC | thiC | |
| 4-Amino-5-hydroxymethyl-2-methylpyrimidine | hydroxymethylpyrimidine kinase | thiJ | 2.7.1.49 |
| 4-Amino-2-methyl-5-phosphomethylpyrimidine | Phosphomethylpyrimidine kinase | thiD | 2.7.4.7 |
| 2-Methyl-4-amino-5-hydroxymethlpyrimidine diphosphate | Thiamine-phosphate diphosphorylase | thiE | 2.5.1.3 |
| Thiamine phosphate | Thiamine phosphatase | | 3.1.3.— |
| Thiamine | | | |

TABLE 3

Synthesis of Pantothenate (Vitamin B5) and Coenzyme A

| Substrate/Product | Enzyme | Gene | E.C. |
|---|---|---|---|
| Pyruvate | acetolactate synthase | ilvB | 2.2.1.6 |
| 2-Acetolactate | ketol-acid reductoisomerase | ilvC | 1.1.1.86 |
| 2,3-Diydroxy-3-methylbutanoate | dihydroxy-acid dehydratase | ilvD | 4.2.1.9 |
| 3-Methyl-2-oxobutanoate | 3-methyl-2-oxobutanoate hydroxymethyltransferase | panB | 2.1.2.11 |
| 2-Dehydropantoate | 2-dehydropantoate 2-reductase | panE | 1.1.1.169 |
| Pantoate | pantoate--beta-alanine ligase/cytidylate kinase | panC/cmk | 6.3.2.1/ 3.5.1.22 |
| Pantothenate (Vitamin B5) | pantothenate kinase | coaA | 2.7.1.33 |
| D-4'-Phosphopantothenate | Phosphopantothenoylcysteine decarboxylase/phosphopantothenate-cysteine ligase | coaBC | 6.3.2.5 |
| 4'-Phosphopantothenol-L-cysteine | Phosphopantothenoylcysteine decarboxylase/phosphopantothenate-cysteine ligase | coaBC | 6.3.2.5 |
| 4'-Phosphopantetheine | pantetheine-phosphate adenylyltransferase | caoD | 2.7.7.3 |
| Dephospho-CoA | dephospho-CoA kinase | coaE | 2.7.1.24 |
| Coenzyme A (CoA) | | | |

TABLE 4

Synthesis of Tocopherol (Vitamin E)

| Substrate/Product | Enzyme | Gene | E.C. |
|---|---|---|---|
| Steroid Biosynthesis | | | |
| Farnesyl-diphosphate | Farnesyltranstransferase | | 2.5.1.29 |
| All-trans-Geranylgeranyl-diphosphate | geranylgeranyl reductase | | 1.3.1.— |
| Phytyl-diphosphate | Homogentisate Phytyltransferase | HPT | |
| 2-methyl-6-phytyl-1,4-benzoquinone | MPBQ/MSBQ methyltransferase | | 2.1.1.— |
| 2-Methyl-6-phytylquinol | tocopherol cyclase | VTE1 | |
| Gamma-Tocopherol | tocopherol O-methyltransferase | G-TMT | 2.1.1.95 |
| Alpha-Tocopherol (Vitamin E) | | | |

TABLE 5

Synthesis of Leucine

| Substrate/Product | Enzyme | Gene | E.C. |
|---|---|---|---|
| Pyruvate | acetolactate synthase | ilvB/ilvH/ilvN | 2.2.1.6 |
| 2-acetolactate | ketol-acid reductoisomerase | ilvC | 1.1.1.86 |
| (R)-2,3-dihydroxy-3-methylbutanoate | dihydroxy-acid dehydratase | ilvD | 4.2.1.9 |
| 2-oxobutanoate | 2-isopropylmalate synthase | leuA | 2.3.3.13 |
| (2s)-2-Isopropyl-malate | 3-isopropylmalate dehydratase | leuC/leuD | 4.2.1.33 |
| (2R,3S)-3-Isopropylmalate | 3-isopropylmalate dehydrogenase | leuB | 1.1.1.85 |

TABLE 5-continued

Synthesis of Leucine

| Substrate/Product | Enzyme | Gene | E.C. |
|---|---|---|---|
| 4-Methyl-2-oxopentanoate | branched-chain amino acid aminotransferase | ilvE | 2.6.1.42 |
| Leucine | | | |

The expression cassette can be expressed via an extrachromosomal DNA such as a plasmid or integrated into the genome by "knock in" methods that are known in the art. A useful general scheme is shown in FIGS. 2A-2C and 3A-3C. The "knock in" of the sequence encoding a selectable marker together with a sequence encoding a protein of interest can be accomplished so that the nucleic sequence encoding the product of interest is in close proximity to the nucleic acid sequence encoding the selectable marker. The two sequences thus become genetically linked (e.g., not separable by genetic recombination).

There may be an intervening nucleic acid sequence connecting the nucleic acid sequences encoding the protein of interest and the selectable marker and this intervening nucleic acid sequence may vary in sequence and/or size. For example, the intervening nucleic acid sequence may be at least or about 100, 200, 300, 400, 500, 600, 700, 800, 900, or 1000 by in length (or any other integer value, including integer values between the values stated here). For example, the intervening nucleic acid sequence may be at least or about 110, 120 or 130 bases long or between 1,000 to 10,000, 1,000 to 5,000, or 1,000 to 2,000 bases in length.

The expression cassette is designed so that the product of interest (e.g., an mRNA or a protein of interest) and the selectable marker are expressed, carrying any necessary sequence elements that are required for expression of the product of interest and the selectable marker (e.g., promoter elements, terminator elements, elements required for translation of an RNA, elements required for stability of an RNA, or elements required for RNA processing).

In some embodiments, transcription of the product of interest and the selectable marker initiates from a single promoter and the nucleic acid sequences encoding the product of interest and the selectable marker are on single RNA. In some embodiments, translation of a protein of interest is coupled to translation of the selectable marker. For example, the amino acid sequence of the protein of interest may be joined to the amino acid sequence of the selectable marker to produce a fusion, or hybrid, protein. Alternatively or in addition, the protein of interest may be fused to a heterologous protein sequence. For example, where the protein of interest is an immunogen, it may be fused to all or a portion of a heat shock protein.

Positive selectable markers from the vitamin B12 synthetic pathway are shown in FIG. 5. Vitamin B12 is a complex coenzyme synthesized only in certain soil and water bacteria and is a critical dietary nutrient for all mammals. As it is produced in two pathways that are dependent on thirty enzymes, it is highly suitable for multiple targeting and replacement events, creating multiple selection processes. As the product of successful selection is vitamin B12, the engineering process will not create an organism with potentially detrimental characteristics. As many of the enzymes are linked within a small area of the bacterial chromosome, multiple genes can be easily removed by targeted integration. If plasmids that contain genes for the vitamin B12 enzymes and our desired engineered protein are added, daughter organisms that produce the engineered protein can be isolated by selecting in vitamin B12 deficient media. Although in the first instance, the engineered proteins are envisioned to be metal binding proteins, in fact this process could be used to introduce multiple enzymes into cells in a stable manner, as discussed through the present specification. These enzymes could catalyze any of the multiple steps in any industrial process, including the production of chemical entities such as ethanol or the destruction of contaminating proteins, fats or chemicals to assist in their removal from air, soil or water. As noted, the present methods are especially beneficial where the waste products of the reaction will not contain antibiotic residue.

The positive selectable marker that can be used as part of the protein expression system described herein can, when introduced in a functional way into a mutant cell requiring a particular essential nutrient, restore the capability of that mutant cell to survive in a growth environment (e.g., in a natural environment or in media) that is not supplemented with the essential nutrient. The ability of the positive selectable marker to restore viability to the mutant cell is termed "complementation."

In some embodiments, the positive selectable marker to be used with a particular mutant strain is a nucleic acid encoding a wildtype version of an endogenous protein of the mutant strain that is either mutated, or not expressed. In some embodiments, the positive selectable marker to be used with a particular mutant strain is a nucleic acid encoding a protein that acts downstream (in an enzymatic pathway) of an enzyme or component that is mutated in the mutant strain. Any nucleic acid can be used as a positive selectable marker with a particular mutant strain so long as it complements the viability defect of that mutant strain in a genetic complementation test, a method which is well known in the art. A positive selectable marker to be used with any particular mutant strain can be identified by performing a genetic complementation test or screen, methods which are well-known in the art.

Linkers, Cleavable Linkers:

A number of peptide linkers can be used to link the protein of interest to the selectable marker protein. In some embodiments, the linker may act as a hinge, allowing greater flexibility so that the protein of interest and the selectable marker protein retain biological activity. For example, the peptide linker can include one, two, three, four, five, six, seven, eight, nine, ten, twenty, thirty, forty, fifty, sixty, seventy, eighty, ninety, one-hundred or more amino acids. In some embodiments, the linker contains amino acids that are more likely to adopt flexible conformations, e.g., comprising glycine, alanine, and/or glutamine residues.

In some embodiments, the linker is cleavable. For example, the hinge may contain a protease enzyme site so that after a hybrid protein is produced, the two domains can be separated within the cell to operate independently. In another example, the hinge may contain a protease enzyme site so that the two functions can be separated at any stage of isolation and/or purification of the hybrid protein or the protein of interest interest.

Tags:

A protein of interest can be expressed as a fusion protein in that it includes a purification tag (or epitope tag). The purification tag is bound by an agent that can be employed for isolating or purifying the protein of interest. A monoclonal antibody that binds to the purification tag, or a Nickel containing matrix are examples of agents that can be employed for isolating or purifying a protein of interest that includes a purification tag. The purification tag can be bound onto the N- or C-terminus of the protein of interest. For this purpose, a commercial epitope-antibody system can be utilized (Jikken Igaku, *Experimental Medicine* 13:85-90, 1995). Vectors are commercially available which are capable of expressing fusion proteins with β-galactosidase, maltose-binding protein, glutathione S-transferase, and green fluorescence protein (GFP), for example.

Examples of purification tags include, but are not limited to, polyhistidine (His-tag), influenza hemagglutinin (HA), human c-myc, FLAG, Vesicular stomatitis virus glycoprotein (VSV-GP), T7 gene 10 protein (T7-tag), human herpes simplex virus glycoprotein (HSV-tag), and E-tag (epitope on the monoclonal phage). Monoclonal antibodies that recognize these epitopes are known in the art (Jikken Igaku, *Experimental Medicine* 13:85-90, 1995). Some of these and other tags are discussed further below.

The protein of interest can be isolated or purified by immunoprecipitation. In immunoprecipitation, immune complexes are formed by adding antibodies recognizing the protein of interest (or purification tag) to a cell lysate. This immune complex can include the protein of interest and an antibody. Immunoprecipitation can be performed using an antibody to a protein of interest or an antibody that binds the purification tag.

Immune precipitation, in general, may be carried out according to or following the method described by Harlow and Lane (*Antibodies*, pp. 511-552, Cold Spring Harbor Laboratory publications, Cold Spring Harbor, N.Y., 1988).

In addition, proteins with purification tags may be isolated or purified by affinity chromatography.

Cells that produce higher levels of metal sequestering proteins will be useful in sequestering more toxic metals within themselves and out of the wider environment. However selected amino acid additions to the metal sequestering proteins themselves would create proteins that can more easily be isolated away from the rest of the cell products. This extra layer of concentrating the proteins with their bound metals will add another layer of improvement to the process. As noted above, a useful molecular tag is a string of histidine amino acids. This His-tag has a high affinity for nickel so proteins engineered to have this added amino acid sequence can be isolated by adding a solution of lysed cells or media to a nickel covered column or surface and washing away everything that has not bound. Little will remain other than the His-tagged protein. Many other tags have been developed that can be added at either end of the engineered protein and a few that can be added in the middle. Examples include the maltose-binding protein (MBP) that binds to amylose and a section of the human immunoglobulin IgG constant region that will bind Protein A. Other tags are protein sequences that bind a specific antibody. An example includes the Myc tag isolated using anti-Myc antibodies. The selection of tag is determined by factors including flexibility of protein, method of protein production and desired method of protein purification. Some tags can include sites for simplified separation from the rest of the protein. In this invention, protein tags are added to the metal sequestering proteins, the joint metal sequestering and restriction marker protein and the metal co-factor requiring protein. In all these cases, the cells will absorb and concentrate metals from their surrounding by producing metal requiring transcription factors and metal sequestering proteins that bind and retain these metals. If these proteins also have tags, they can be easily isolated and concentrated thus concentrating the metals further. These metals can then be more easily removed from the environment.

Nucleic Acids:

The invention also encompasses nucleic acid molecules that constitute the expression cassettes described herein and encode the polypeptides of interest and selectable markers. Expression cassettes, vectors (e.g., plasmid vectors) including them, and host cells containing them are all aspects of the present invention. The nucleic acids encoding biologically active variant polypeptides can be similarly described as having at least or about 25%, 50%, 65%, 75%, 80%, 85%, 90%, 95%, 96%, 97%, 98%, or 99% identity to a corresponding naturally occurring nucleic acid sequence. Those of ordinary skill in the art will readily recognize degenerate variants of nucleic acid sequences, and such variants can be used for the purposes described herein.

The nucleic acid molecules that encode the polypeptides described herein may be codon optimized for expression in a particular host cell type. For example, a nucleic acid sequence encoding a protein from *Zea mays*, such as zein, may be altered to contain codons that are preferably used in cyanobacteria host cells. In another example, a nucleic acid sequence encoding a human protein may be altered to contain codons that are preferably used in *E. coli* or *S. cerevisiae* host cells. Methods for codon optimization are known in the art.

The invention also features vectors that include the present nucleic acid constructs (e.g., expression cassettes). Of particular benefit are expression vectors for expression in prokaryotic and eukaryotic cells. Such vectors can, for example, be viral, plasmid, cosmid, or artificial chromosome (e.g., yeast artificial chromosome) vectors.

Typically, plasmids are circular, dsDNA elements that include one or more cloning sites for insertion of selected DNA sequences, e.g., coding sequences. Such plasmids may include a functional origin of replication and thus are replication competent, or may be replication defective.

In addition to plasmids, viral vectors (e.g., replication defective retroviruses, lentiviruses, adenoviruses and adeno-associated viruses) can also be advantageously used. A large number of such viral vectors have been developed having a broad variety of different properties. For example, such viral vectors may be replication defective retroviruses, adenoviruses and adeno-associated viruses. Techniques and procedures for producing recombinant retroviruses and for infecting cells in vitro or in vivo with such viruses are provided in Current Protocols in Molecular Biology, Ausubel, F. M. et al. (eds.) Greene Publishing Associates, (1989), Sections 9.10-9.14 and other standard laboratory manuals. Examples of suitable retroviruses include pLJ, pZIP, pWE and pEM which are well known to those skilled in the art. Examples of suitable packaging virus lines include psi.Crip, psi.Cre, psi.2 and psi.Am.

The genome of adenovirus can be manipulated such that it encodes and expresses a nucleic acid construct, as described herein, but is inactivated in terms of its ability to replicate in a normal lytic viral life cycle. (see, e.g., Berkner et al., *BioTechniques* 6:616, 1988; Rosenfeld et al., *Science* 252:431-434, 1991; and Rosenfeld et al., *Cell* 68:143-155, 1992). Suitable adenoviral vectors derived from the adenovirus strain Ad type 5 d1324 or other strains of adenovirus (e.g., Ad2, Ad3, Ad7 etc.) are well known to those skilled in the art. Alternatively, an adeno-associated virus vector such as that described in Tratschin et al. (*Mol. Cell. Biol.* 5:3251-3260, 1985) can be used to express a transactivator fusion protein. Other viral vector alternatives include lentiviral vectors. Such vectors and their preparation and use are described, for example, in U.S. Pat. Nos. 6,924,123; 6,863,884; 6,830,892; 6,818,209; 6,808,923; 6,799,657, all of which are incorporated herein in their entireties.

The vectors of the invention can advantageously include sequences encoding any of the proteins described herein (i.e., any of the proteins of interest or selectable marker proteins). Other elements included in the design of a particular expression vector can depend on such factors as the choice of the host cell to be transformed, the level of expression of protein desired, etc. The expression vectors of the invention can be introduced into host cells to thereby produce proteins, including fusion proteins, encoded by nucleic acids as described herein.

The vectors described herein can be introduced into cells or tissues by any one of a variety of known methods within the art. Such methods are described for example in Sambrook et al., Molecular Cloning: A Laboratory Manual, Cold Spring Harbor Laboratory, New York (1992), which is hereby incorporated by reference. See, also, Ausubel et al., Current Protocols in Molecular Biology, John Wiley and Sons, Baltimore, Md. (1989); Hitt et al., "Construction and propagation of human adenovirus vectors," in Cell Biology: A Laboratory Handbook, Ed. J. E. Celis., Academic Press. 2.sup.nd Edition, Volume 1, pp: 500-512, 1998; Hitt et al., "Techniques for human adenovirus vector construction and characterization," in Methods in Molecular Genetics, Ed. K. W. Adolph, Academic Press, Orlando, Fla., Volume 7B, pp: 12-30, 1995; Hitt, et al., "Construction and propagation of human adenovirus vectors," in Cell Biology: A Laboratory Handbook," Ed. J. E. Celis. Academic Press. pp: 479-490, 1994, also hereby incorporated by reference. The methods include, for example, chemical transformation, stable or transient transfection, lipofection, electroporation and infection with recombinant viral vectors. The term "transfecting" or "transfection" is intended to encompass all conventional techniques for introducing nucleic acid into host cells, including calcium phosphate co-precipitation, DEAE-dextran-mediated transfection, lipofection, electroporation and microinjection. Suitable methods for transfecting host cells can be found in Sambrook et al. (Molecular Cloning: A Laboratory Manual, 2nd Edition, Cold Spring Harbor Laboratory press (1989)), and other laboratory textbooks.

For plant cells, a Ti plasmid or viral vector is often used. For example, such plasmids and viral vectors can be used to transfect host plant cells via *Agrobacterium tumefaciens*-mediated transfection (for plant cells susceptible to *A. tumefaciens* infection), or can be directly inserted in cells, e.g., using microinjection, particle bombardment, or electroporation. In other methods, protoplasts can be made from plant cells and then transfected.

The number of host cells transformed with a nucleic acid constructs of the invention will depend, at least in part, upon the type of recombinant expression vector and the type of transfection technique used. Nucleic acid can be introduced into a host cell transiently, or for long-term expression. For long-term expression, the nucleic acid is stably integrated into the genome of the host cell or remains as a stable episomal element.

Host Cells and Methods of Making Same:

The present expression cassettes can be used to modify virtually any biological cell. Accordingly, the invention features methods of genetically modifying a cell, which we may refer to as a "host cell" (e.g., cyanobacterium). The methods can be carried out by (a) providing a cell and (b) performing targeted replacement of a nucleic acid sequence within the cell that encodes a positive selectable marker with a nucleic acid sequence that encodes a negative selectable marker. As noted above, the positive selectable marker can be an enzyme within a biosynthetic pathway that produces an essential nutrient and the negative selectable marker can be a protein that confers antibiotic resistance (see also FIGS. 2A, 2B, and 2C). Cells made by this method are within the scope of the present invention as are those that are further modified by (c) performing targeted replacement of the nucleic acid sequence that encodes the negative selectable marker with a nucleic acid sequence encoding (i) a protein of interest and (ii) a nucleic acid sequence encoding the positive selection marker.

Other methods include those of producing a protein of interest in a biological cell using the present expression linked system. These methods can be carried out by (a) culturing a cell made as described above under conditions that permit expression of the protein of interest; and (b) isolating the protein of interest from the cell (e.g., the cyanobacterium).

Depending on the protein of interest, the cells can also be used intact (i.e., without purifying the protein of interest from the cell). For example, where the protein of interest is secreted (with signal sequences included in the expression cassettes to direct the secretion) one may simply bring the cells and/or the media in which they are growing in contact with the source of a protein to be acted on by the protein of interest. The same is true where the cells are modified by the protein of interest in such a way as to sequester or transport substances such as metals or sugars out of the environment.

Accordingly, the invention also features method of removing a metal from a metal-containing material by contacting the metal-containing material with a cell that expresses or secretes a metal-binding protein or with the metal-binding protein per se following its isolation from the cells. The metal-containing material can be soil or water. Alternatively, the metal-containing material can be within a patient, and the metal-binding protein can be administered to the patient.

Other methods of the invention accelerate fructose metabolism by degrading the fructose or sequester it by virtue of intracellular uptake. The method can be carried out by contacting a fructose-containing material with a cell modified as described herein to express an enzyme that accelerates fructose metabolism (e.g., hepatic fructokinase, aldolase B, or glyceraldehyde kinase). The cells can also be modified to alter the amount of fructose in a material by virtue of expressing proteins that facilitate the transport of fructose from the material into the cell. In that event, the protein of interest would be phosphoenolpyruvate-protein phosphotransferase, HPr protein and/or protein-Nπ-phosphohistidine-sugar phosphotransferase (fructose-specific). The combination would create an ATP-binding cassette transporter (ABC transporter) on the surface of the cell that would actively transport fructose into the cells. As noted above, the expression cassettes can include sequences including multiple proteins of interest and/or multiple expression cassettes can be used. In any event, the fructose-containing material can be water.

As noted above, the present expression cassettes can be introduced into prokaryotic or eukaryotic cells growing in culture in vitro by conventional transfection techniques (e.g., calcium phosphate precipitation, DEAE-dextran transfection, electroporation, and other methods). Cells can also be transfected in vivo, for example by application of a delivery mechanism suitable for introduction of nucleic acid into cells in vivo, such as viral vectors (see e.g., Ferry et al., *Proc. Natl. Acad. Sci. USA* 88:8377-8381, 1991; and Kay et al., *Human Gene Therapy* 3:641-647, 1992), adenoviral vectors (see e.g., Rosenfeld, *Cell* 68:143-155, 1992; and Herz and Gerard, *Proc. Natl. Acad. Sci. USA* 90:2812-2816, 1993), receptor-mediated DNA uptake (see e.g., Wu and Wu, *J. Biol. Chem.* 263:14621, 1988; Wilson et al., *J. Biol. Chem.* 267:963-967, 1992; and U.S. Pat. No. 5,166,320), direct injection of DNA (see e.g., Acsadi et al., 991) *Nature* 332:815-818, 1991; and Wolff et al., *Science* 247:1465-1468, 1990) or particle bombardment (see e.g., Cheng et al., *Proc. Natl. Acad. Sci. USA* 90:4455-4459, 1993; and Zelenin et al., *FEBS Letters* 315: 29-32, 1993). Thus, another aspect of the invention pertains to host cells into which an expression cassette has been introduced, i.e., "recombinant host cells." The term "recombinant host cell" refers not only to the particular cell subjected to modification, but also to the progeny or potential progeny of such a cell. Because additional modifications may occur in succeeding generations due to either mutation or environmental influences, such progeny may not, in fact, be identical to the parent cell, but are still included within the scope of the term as used herein.

A host cell can be any prokaryotic or eukaryotic cell. Exemplary eukaryotic cells include yeast cells (e.g., *S. cerevisiae* or *S. pombe*), mammalian cells (such as Chinese hamster ovary cells (CHO) or COS cells).

Exemplary prokaryotic cells include cells of gram-positive and gram negative bacteria. For example, *E. coli* are gram negative bacteria may be used as host cells. In another example, Cyanobacteria may be used as host cells. For example, cyanobacterium of *Anabaena* species (sp.), *Anabaenopsis* sp., *Aphanizomenon* sp., *Arthrospira* sp., *Calothrix* sp., *Chamaesiphon* sp., *Chlorogloeopsis* sp., *Chroococcidiopsis* sp., *Chroococcus* sp., *Cyanothece* sp., *Cylindrospermum* sp., *Dactylococcopsis* sp., *Dermocarpella* sp., *Fischerella* sp., *Geitlerinema* sp., *Gloeobacter* sp., *Gloeocapsa* sp., *Gloeothece* sp., *Leptolyngbya* sp., *Lyngbya* sp., *Microchaete* sp., *Microcoleus* sp., *Microcystis* sp., *Myxosarcina* sp., *Nodularia* sp., *Nostoc* sp., *Oscillatoria* sp., *Pleurocapsa* sp., *Pseudanabaena* sp., *Scytonema* sp., *Spirulina* sp., *Stanieria* sp., *Symploca* sp., *Synechococcus* sp., *Synechocystis* sp., *Tolypothrix* sp., or *Xenococcus* sp may be used.

The host cell may be haploid, diploid, or polyploid. If the cell is diploid or polyploid, the cell may be homoallelic for the one or more mutations that allow it to be used with a particular selectable marker. Other suitable host cells are known to those skilled in the art.

Kits:

The cells made as described above, the expression cassettes, and any associated materials (e.g., cell culture media) can be packaged (singly or in combination with one another) with instructional materials (e.g., printed materials) for distribution and use as a kit.

Methods of Use:

Bioremediation:

Environmental contamination by toxic metals including, but not limited to, lead (Pb), cadmium (Cd), silver (Ag), gold (Au), mercury (Hg), thallium (Ti), nickel (Ni), and platinum (Pt) has and will continue to be a problem. For example, lead released into the air as a result of the burning of coal in industrial plants, is a major cause of acid rain. Cadmium (which is also released when coal is burned) is also problematic given it's high toxicity. In addition, metal contaminated soil is adverse to human health. Current industrial practices produce contaminated material which is expensive to remove and store. Current methods of removing metals from the contaminated air, soil and water are cost prohibitive, especially when the metals are at low concentrations (below 50 mg/L) or less. In addition, some methods of removing metals from an environment are difficult and dangerous and these drawbacks outweigh the benefits of removing the metals. An example of this is the removal of lead from soil that has been contaminated by lead paint or industrial processes.

Currently existing bioremediation methods to, for example, remove contaminating metals from air, soil and water rely on using dead biomass such as straw or live microorganisms. These methods are limited in that they often fail to reduce metal concentrations to acceptable, non-toxic levels in part because the organisms employed in some of these methods are inviable or non-functional in high concentrations of metals. In addition, current methods do not always concentrate the metals sufficiently for easy and cost-effective removal. For example, straw can be used to absorb toxins from water, but the contaminated straw is bulky, difficult to handle, and difficult to separate from contaminating metals. In addition, burning of contaminated straw, while reducing mass, releases metals into the atmosphere. New methods to safely remove contaminating metals from the environment are needed to avoid toxic chemical processes and to reduce contaminating metals to non-toxic concentrations in the environment.

The methods described herein are useful in creating genetically modified organisms that in order to be viable, express metal binding proteins, thus coupling their viability to an increased capacity to acquire and store metals. Thus, these genetically modified organisms acquire and store metals with great efficiency. The methods of this invention also include those for separating metals from biomass (e.g., the genetically modified organisms) by isolating metal binding proteins that are bound to the contaminating metals.

The present invention addresses the problem of efficient methods to remove metals from surrounding material such as water, gas or soil.

Methods of Collecting Valuable Metals:

Some valuable metals such as gold exist at low concentrations in mined material and toxic means are frequently used to isolate and purify them. The methods described herein can also be used to isolate and purify valuable metals. These methods have the advantage of being non-toxic.

Most organisms from simple bacteria, algae, fungus and yeast through advanced plants, insects and animals use metals as part of their metabolic processes. Genomic analysis suggests that as many as one third of proteins require a metal co-factor for effective function. Sodium (Na) Calcium (Ca) and Potassium (K) are critical for nerve function. Iron (Fe) is the metal cofactor in hemoglobin and without it hemoglobin is unable to transport oxygen around the body. Zinc (Zn) is a critical trace element for life due to it ability to stabilize zinc finger domains. These domains are small stretches of amino acids that form two antiparallel β strands and an α helix that require the metal ion to remain properly folded. When properly folded, this protein domain can bind to DNA. Zinc finger domains occur in many transcription factors and other genetic modulators. Many other cellular functions use a metal as important cofactors for the operation of proteins.

To support their need for some metals, cells will actively transport and store critical ones. As many of these metal binding proteins cannot always distinguish between metals of similar charge (i.e. toxic Cadmium instead of critical Zinc), toxic metals will also be acquire and stored, resulting in metal toxicities. One example is the acquisition and storage of mercury in critical tissues such as the brain, resulting in mercury poisoning. If organisms are forced to exist in an environment that contains elevated levels of metals, the cells will respond by producing higher levels of protective metal storage proteins. These proteins such as metallothionein will bind the metal and prevent its interference with critical cellular pathways.

Bioremediation has long been suggested as a method to safely remove contaminating metals from soil and water. The methods have included using dead biomass such as straw or live micro-organisms such as cyanobacteria. These methods do have limited success but more efficient ones are required. Some needed requirements include the ability to function in high concentrations of metals and also reduce metal concentration below toxic level. In addition, current methods do not always concentrate the metals sufficiently for easy removal of the metal from the rest of the remedial biomass. For example, straw can be used to absorb toxins from water but the contaminated straw has a large bulk that is difficult to handle and difficult to separate from the metals. The process of burning the contaminated straw will reduce the total mass and concentrate some of the metal but other metal ions will be released into the atmosphere in the exhaust gas.

Therefore new methods to safely remove contaminating metals from the environment are needed. These methods need to avoid toxic chemical processes and be able to reduce the metals to non-toxic concentrations in the environment. If safe organisms can be created to have as part of their life cycle the critical need for metals, in response they will acquire and store these metals with great efficiency. If this method also includes methods to separate the organisms and their metal containing proteins, another layer of save metal concentrating will be included. The final result will be a biologically safe and cost effective way to remove toxic, valuable or radioactive metals from the environment.

The present invention addresses the problem of efficient methods to remove metals from surrounding material such as water, gas or soil. It describes methods to speed the evolution of efficient metal binding proteins and methods to identify and isolate them. It describes methods to identify the coding and flanking DNA sequences of the metal sequestering proteins so they can be used in engineered processes. The invention describes methods to identify and isolate transcription factors that require metal co-factors and methods to identify DNA promoter sequences that bind these transcription factors. The invention describes how to use the DNA of known and newly isolated metal sequestering proteins to create different cells types including bacteria through mammalian that can efficiently grow in high metal solutions by safely sequestering those metals within themselves. It improves the production of these metal sequestering proteins by linking their transcription to a selectable marker either as two separate DNAs transcribed from a single promoter or as a single protein of two parts, part metal sequestering domain linker to the selectable marker enzyme domain. Another version of this invention also adds a molecular tag to the metal sequestering domain to improve methods to purify the metal sequestering protein along with its bound metal. A final section of this invention describes how to use transcription factors that require a bound metal ion for function and use their specific DNA promoter to drive the translation of a selectable marker, metal sequestering protein or both. A cell containing this DNA construct would only survive in selection media if it is able to obtain the necessary metal ion. This would result in a high demand by the cells for the metal ions, resulting in a greater sequestering of metals within the cells. As current bacterial selection systems are all based on resistance to antibiotics and safer selection is needed, part of this invention describes the development of a positive selection based on removing and then replacing the cells ability to produce the critical nutrient Vitamin B12 (cobalamine). Because different conditions could occur, this invention describes how to use this process to create systems that would work in a wide variety of cells from bacterial through mammalian.

The overall results of this invention is to create cells that 1) have the ability to produce proteins that efficiently sequester metals; 2) produce proteins that while binding the metals, can be easily isolated from the rest of the biomass; 3) are under strong selective pressure to produce offspring that have the same characteristics; 4) require metal to survive and thus will deplete surrounding metals to a very low level; and 5) is desired, could use the production of Vitamin B12 for the selective pressure.

Adapting Bacteria to High Levels of Metal:

Many bacteria that grow in water or soil have the ability to survive relatively high concentrations of metals including lead (Pb), nickel (Ni), zinc (Zn) and chromium (Ch). They survive these normally toxic levels by producing proteins that bind and sequester these metals. An example of such proteins is metallothioneins. Metallothioneins are small cysteine-rich proteins produced by a wide variety of cells including bacteria, cyanobacteria, insect, bird, fish, bivalve, plant, mammals and others. They bind a wide variety of toxic and non-toxic metals and allow cells to safely absorb and bind metals so the metals are not able to interfere with normal cellular process. This invention describes the method to evolve and isolate proteins and their encoding DNA that have are most effective at binding different metals. To find the exact protein that has the greatest ability to bind and sequester these metals, any number of cell types from many life forms could be put under selective pressure in metal containing solutions to push the mutational process for new sequences of these proteins. These metals could be one or more including lead (Pb), cadmium (Cd), silver (Ag), Gold (Au), Mercury (Hg), Thallium (Ti), Nickel (Ni), Platinum (Pt) and others.

As these proteins occur in many bacteria and higher forms of life, the selection is infinite and would likely be narrowed only by the researcher's preference. Cyanobacteria, also known as microalgae or blue-green algae, could be used in one example to isolate the desired proteins because they have robust growth profiles and the ability to survive in bright light and a wide variety of conditions. There are nearly 3000 species that have been classified and they have been isolated from environmental conditions as diverse as the sea around Antarctica to the steam vents at Yellowstone Park. They exist in virgin, contaminated and barren soil. They grow in salt water, brackish water, spring water and fresh water. Their most common presentation to people is in the form known as pond scum. Although they are single cell organisms, they can exist in large colonies and one of their great strengths is their ability to uses photosynthesis to convert sunlight into energy and use this energy to drive their production of proteins and fats. This ability to produce high quality fats has made cyanobacteria high desirable in the production of raw material for biodiesel. As some of their living conditions have been contaminated with high levels of metal, many cyanobacteria have developed methods to survive these conditions.

Many forms of bacteria that do not have the ability use photosynthesis also exist. They have been isolated both from the environment and within other organisms where they live in neutral, beneficial and pathogenic symbiosis. Like the cyanobacteria, many other forms of bacteria have developed methods to survive in high levels of metal and thereby have carved out an environment in which they have reduced competition for resources. Many strains of bacteria and cyanobacteria could be obtained from any environmental source that may be contaminated with the preferred metal or not. Many can be obtain from different sources such as the ATCC.

A quick search of bacteria or cyanobacteria that were isolated from soil or water from various locations around the world returns a list of hundreds of possibilities. They could include the following but are not limited to these listed in Table 6.

TABLE 6

Representative Cyanobacteria and Bacteria Isolated from Water or Soil

| Cyanobacteria/Blue-Green Algae | Bacteria without Photosynthesis |
|---|---|
| *Anabaena* sp. | *Acidovorax facilis* |
| *Calothrix* sp. | *Azotobacter vinelandii* |
| *Chaemisiphon* sp. | *Brevundimonas variabilis* |
| *Chlorogloeopsis* sp. | *Derxia gummosa* |
| *Chroococcidiopsis* sp. | *Enterococcus haemoperoxidus* |
| *Cylindrospermum* sp. | *Flavobacterium* sp. |
| *Fischerella* sp. | *Kocuria rosea* |
| "*Geitlerinema*" sp. | *Micrococcus luteus* |
| *Nostoc* sp. | *Planococcus* sp. |
| *Oscillatoria* sp | *Pseudomonas* sp. |
| *Synechococcus* sp. | *Sarcina ventriculi* |
| *Synechocystis* sp. | *Staphylococcus* sp |
| *Tolypothrix* sp | *Terracoccus luteus* |

The ability to survive in metal contaminated environments is not limited to bacteria. Many examples exists of yeast, insects, fish, bivalves, birds, plants, mammals and others increasing their levels of metal sequestering proteins such as metallothioneins when such organisms are forced to live in metal contaminated environments. Using the methods described in this invention, proteins with improved metal sequestering abilities could be identified in any life form.

Developing Improved Metal Sequestering Proteins:

Some organisms already have the ability to survive high levels of metal in their environment but in selective conditions could improve their toleration levels. Others have little initial tolerance of metal contaminates but can rapidly adapt. For this reason, the source and number of organisms that are put through the process of metal adaptation is dependent on the preference of the researcher. The process involves growing the cells in increasing concentration of the metal of choice. This will result in the cells that can adapt to survive and produce more offspring. The initial concentration used in the adaptation process for Lead would be equal to or less than 1 mg/L Lead. With other metals, especially the more toxic ones such as Cadmium or Gold, the starting concentration should be lower. This initial selection could be conducted in many different life forms although the rapid growth of bacteria may make the process faster. Once the initial selection to determine those most likely to rapidly adapt to toxic metals is completed, the metal concentration can be gradually increased. This will be a simple process of growing the bacteria or other cells in their recommended conditions for media, temperature and other growth conditions. The purpose of this process is to create metal binding proteins whose DNA will be transferred to a cell of choice so cell growth conditions in this process are not likely to effect final conditions of use. As the metal concentrations are increased, the growth rates of the cells should be assessed. There will be an initial lag in cell growth that will recover as the bacteria or other cells ramp up their production of protective metal absorbing proteins. As a control to allow isolation of the gene for the protective protein, cells are also grown in matching conditions without the added metal. This process should continue until the bacteria can no longer tolerate increasing concentrations of metal. For a metal such as lead, this will be greater than 50 mg/L and could easily be 5-10 times that amount. Tolerable concentration of other metals will vary with their intrinsic toxicity.

Comparison of the differences in protein and RNA between the metal adapted and non-adapted cells will allow the isolation of DNA for proteins with potentially improved metal sequestering abilities. Some proteins could be found that reduce the cells' capacity for metal sequestration. In these circumstances, processes could also be developed to remove or reduce their function.

Transcription and Metal Co-Factor Containing Transcription Factors:

Proteins are produced by cells in a series of highly regulated steps. In the most basic form, the gene for a protein contains the actual coding region. This is flanked upstream by a promoter sequence, an area of DNA that binds to specific transcription factor proteins. The gene is also flanked downstream by a termination or polyadenylation sequence, a DNA sequence encoding RNA that triggers the addition of a protective RNA tail. The transcription of the specific coding RNA is triggered by the binding of transcription factor proteins to the promoter region which starts the actions of the RNA polymerase machinery. Without properly produced and folded transcription factor proteins, the specific gene will only be transcribed into RNA for later proteins translation at a very low level if at all. Many transcription factor proteins require a metal ion for proper folding before it can bind to its specific DNA and trigger transcription. If this protein encodes part of a critical pathway for the cell and the cell cannot make a fully functioning protein, the cell will not survive. For this reason, cells are under great evolutionary pressure to preserve the accurate promoter region, produce the appropriate transcription factor and acquire any metal co-factors needed for the transcription process. The simplest systems control gene transcription function in bacterial cells. These systems tend to be more complex in yeast, insects, fish, plants and mammals although the need for metal cofactors remains. The process of transcription and translation can also be reconstituted in cell free systems if all the necessary components are added including the necessary metal cofactors.

Cloning Improved Metal Sequestering Proteins:

By comparing the protein and RNA difference between the metal adapted and non-metal adapted bacteria by standard techniques including protein gels, negative hybrid and other molecular techniques well known to those versed in the art, the critical metal binding proteins produced by the metal adapted bacteria can be easily isolated. The difference in the RNA expression between the adapted and non-adapted bacteria and comparison of this with the protein information will allow for the creation of a cDNA construct encoding the necessary protein or proteins for bacteria cell survival in high metal concentrations. Some of these survival adaptations will include increased ability to export the metals from the cells (not desired for this invention) and others will include proteins that bind metals with increasing avidity. The proteins that bind the metals are the desired outcome of this invention although other proteins that assist in the production and function of these metal binding proteins are also useful for this invention. Some of these may include transcription and chaperone proteins. In addition, the information about the DNA promoters for the genes of interest should be determined and compared with known sequences to determine if critical mutations have occurred within the promoters that improve the production of metal sequestering proteins.

To compare the effectiveness of these the cloned metal binding proteins, the genes are cloned with identical genetic structure and expressed in similar bacteria cells. Using cloning methods well known in the art, these proteins are functionally linked to a lacA or other promoter and a termination sequence. To determine which of these proteins is most efficient at binding which metal, these constructs are used to transform one or more laboratory bacterial strains such as *E. coli* although a cyanobacteria could also be used. Clones are grown in increasing levels of toxic metals to determine which protein tends to sequester the metal most efficiently. This selection process will rapidly determine which DNA construct is most able to give the bacteria a selective advantage for each metal. In addition to identifying the metal binding capacities of the isolated proteins, this process could create bacterial strains that can be used in industrial processes.

If other cells such as insect, yeast, plant, bird, fish, mammal or other types are desired for the bioremediation process, the genes are functionally linked to promoters and terminators or polyadenylation sequences for that type of efficient transcription. They would be tested in the appropriate cell type under similar metal selection to determine the best candidate gene.

Combining Metal Sequestering Proteins with Selectable Markers:

Selectable markers are protein products that allow bacterial or mammalian cells to grow in conditions that are toxic for cells that do not have the gene. An example is the gene for resistance to ampicillin that allows transformed bacteria to grow in the presence of the antibiotic. In this invention, a construct will be made that has the lacA or other promoter functionally linked to the DNA encoding the metal sequestering protein linked to the gene for β-lactamase followed by the lacA or other termination sequence. There will not be a promoter preceding the β-lactamase gene nor termination sequence following the metal sequestering protein gene. This configuration will result in the transcription of a single RNA species that encodes both the metal sequestering protein and the protein that confers ampicillin resistance. For the cells to survive when grown in ampicillin containing media, they will need to transcribe both RNAs. This will tend to increase the expression of the metal sequestering protein. This process could be used in any negative or positive selection system such as that described for Vitamin B12 production and can be tailored to any cell type or grow conditions.

Creating Single Protein with Metal Binding Domain and Selectable Marker:

Creating a situation in which the transcription for the metal sequestering protein and the selectable marker are driven by a single promoter will greatly increase the chance that RNA encoding the metal sequestering protein will be transcribed. Although this will tend to improve the chances the metal sequestering protein will be translated, these chances can be greatly improved if the two functions, metal binding and selectable marker, are included on a single protein. This can be created by combining the coding regions for these two proteins into a single protein. There are many ways to do this but one of the most successful is through the use of a protein hinge. These can be composed of many sequences but one example frequently used to link two antibody variable regions in scFVs produced in antibody phage libraries is composed of three tandem repeats of the sequence Glycine-Glycine-Glycine-Glycine-Serine. The great flexibility of this hinge place between two protein domains means that although these two domains are part of the same protein, they have the ability to flex and operate independently. As the selection marker domain must be produced for the cell to survive, linking the two domains together results in the metal sequestering domain being produce at an equal rate. This also means that the cells can be pushed to produce more metal sequestering protein by adding a higher dose of selection to the growth media.

Isolating Transcription Factors with Metal Cofactor and Associated Promoters

Many transcription factors require metal co-factors for correct folding. Without the metal stabilizing their configuration, they are not able to bind to their designated DNA promoter region. Part of this invention describes methods to isolate transcription factors that can use metals such as Lead and Cadmium as their co-factors. These proteins would then be produced in standard protein expression systems with the exception that the metals added to the system would be the toxic metals to be removed in the bioremediation processes. These transcription factors with their metal co-factors can then be used to identify their preferred DNA promoter regions. This combination of transcription factor and preferred promoter could be used to put cells under high pressure to acquire metals from their surroundings especially if the preferred promoter is used to drive transcription of the selectable marker. The only way the cells could survive in selection media is to transcribe the selectable marker gene. This will only occur when the promoter is bound to its transcription factor. In this case, the transcription factor requires a metal co-factor to properly bind to the promoter so the cells will only survive if they can get the metal co-factor. This selective strong selective pressure will promote the cells removing all potential metals from their surrounding, including the toxic metals.

Creating Metal Sequestering Proteins with Tags and Selectable Markers that are Driven by Metal Cofactor Transcription Factors:

Many of the individual part of the invention can be combined into the creation of cells that are highly efficient and driven to remove metals from their surroundings. The most detailed combination would have the final protein product be composed of the hybrid protein that includes the metal sequestering domain connected to the selectable marker. As this protein would also have a molecular tag that will simplify protein isolation, it creates a system for efficient metal isolation. If the production of this protein is driven by a promoter/transcription factor combination that require a metal co-factor, the cells will be under the highest pressure to subtract metals from their environment and sequester them for critical survival pathways. This will result in a system that has the ability to reduce the concentration of contaminating metals to very low levels.

Using the combination of metal sequestering proteins and metal co-factor requiring transcription factors, many systems can be created to remove toxic metals from the environment. The systems could be based on single cell systems seen in bacteria or cyanobacteria cultures. If needed, they could also be based on insect, yeast or mammalian cell systems. They could also be used within organisms such as intact growing plants. Single cell systems using cyanobacteria may be very useful in cleaning pools of water or exhaust gases from an industrial stack. Plants may be more useful in concentrating radioactive metals from contaminated soil especially in circumstance that frequent human attention is not available. Mammalian cell based systems could be used if the metals are using in one step of a pharmaceutical production process and need to be removed before creation of the final drug. In certain circumstances, the purified metal sequestering proteins can isolated from their production system and used to bind the metals in a cell-free system. The size of the reactions could be on a small laboratory scale of a few milliliters up to the size of large industrial manufacturing scale of millions of liters. It is only limited by the size and scope of the desired circumstances.

To keep the cells at a high density but growing rapidly, cells and protein should be periodically harvested. In addition, more metals could be removed from solution if the bioreactors are set up in series with material to be purified moved through the different reactors. If different proteins are developed with different affinities for different metals, reactors could be arranged so that different metals are removed at different stages (i.e. reactor 1—zinc; reactor 2—lead; reactor 3—cadmium etc). In addition sequential reactors will allow the removal of undesired metals first with subsequent reactors harvesting beneficial ones (i.e. reactor 1—mercury; reactor 2—lead; reactor 3—beneficial micronutrient cobalt bound to Vitamin B).

The process involves combining the desired selection marker, metal sequestering protein, protein tag, metal co-factor requiring transcription factor and its preferred promoter into a single DNA fragment by standard cloning processes. This is introduced into the desired cell type by conditions standard for that cell. The individual cell clone with the desired characteristics is selected and expanded for use. Other combinations can be created depending on the desired bioremediation processes.

One purpose of this invention is to allow the creation of cells that are forced to produce the metal sequestering protein in order to survive. The high affinity of the protein for metals will result in a majority of the metal (Lead, Cadmium etc) being absorbed into the cells and stored within its proteins. As more cells grow, more protein is produced and even if the cells die, the released protein will continue to absorb the metal from the surrounding solution. The cells and proteins can be removed from the solution by centrifugation and protein separation allowing easy capture of the bound metals. This concentration process will create material with a sufficiently high concentration of metal that it can be mined from this material by more simple means.

A second purpose of this experiment is the creation of a non-antibiotic based selection system for bacteria. The process of disrupting enzymes within the Vitamin B12 production pathway along with the reintroduction of the same enzyme along with addition desired genes creates a save selection system that is unlikely to damage animal or human health.

EXAMPLES

Example 1

Isolating Effective Bacterial Sourced Metal Sequestering Proteins

Two cyanobacteria strains, *Synechocystis* sp. (ATCC #29108) and *Anabaena cylindrical* (ATCC #27899), are grown under normal conditions in ATCC (American Type Culture Collection) medium 616 (BG-11 medium for blue-green algae) in shaker flasks at 26° C. under light intensity of 2,000-3,000 lux. *Synechocystis* sp. was isolated from brackish water, and *Anabaena cylindrica* was isolated from pond water (both are available from the ATCC). Normal growth curves for each bacterium are established through standard division and determination of optical density.

Both strains are put under selective pressure by growing samples in similar conditions with the addition of lead (Pb) or cadmium (Cd). Ideally, the starting concentration of both metals is 1 mg/L, although it may be necessary to start at a lower concentration of cadmium. In addition to the metal growth solutions, samples of each bacterium are grown in the standard media. To put the selecting cells under greater pressure, the levels of trace metals standard in ATCC medium 616 (manganese (Mn), zinc (Zn), molybdenum (Mo), copper (Cu) and cobalt (Co)) should be reduced to force greater reliance on the contaminating metals (Pb and Cd).

As the concentration of metal is increased, there is an initial lag in cell growth that recovers as the bacteria ramp up their production of protective metal sequestering proteins. The growth rates are followed and once the bacteria are growing well, a sample of each strain is transferred to media with two times, four times or eight times the concentration of metal. As the growth rate stabilizes, the metal concentrations are again increased. After each recovery step, samples of the bacteria are frozen for storage and later analysis. This process is repeated until the bacteria cannot tolerate higher metal concentrations. With Pb, this is greater than 50 mg/L and could be as high as 500 mg/L. The tolerable levels of Cd are lower.

RNA, genomic DNA and protein are isolated from the bacterial samples by standard techniques. By comparing the difference between protein and RNA in the metal adapted and non-metal adapted bacteria, which can be done with standard techniques including protein gels, negative hybrid, expression analysis, TGGE and other molecular techniques well known in the art, the critical metal-binding proteins produced by the metal adapted bacteria can be easily isolated. These proteins can be expressed from both upregulated genes and mutated genes. Differences in the RNA expression between the adapted and non-adapted bacteria and comparisons of this with the protein information allows for the creation of a cDNA construct encoding the necessary protein or proteins for bacterial cell survival in high metal concentrations. The proteins of interest for this example will include those that have sequences similar to those of known metallothioneins. The protein information is compared with the isolated RNA species to select the desired coding sequences. With homologous and random primers, PCR reactions using genomic DNA as a template can create DNA constructs that encode the metal sequestering coding region flanked by its particular promoter and termination sequences. These flanking sequences may allow a higher rate of gene transcription than other promoter/termination sequences.

To compare the relative abilities of the isolated metal sequestering proteins to bind contaminating metals, vector constructs are made to test the respective genes in bacterial and mammalian expression systems using standard cloning methods. For the bacterial cell tests, the DNA coding regions can be functionally linked to the lac operon promoter and terminator. FIG. 1 is a schematic diagram of the functional region. As a comparison, the coding sequences of known metallothioein genes from other sources can also be tested in these vectors. These genes include, but are not limited to, the trout Cd/Zn MT, human MT2A, cyanobacteria SmtA and others, including the bacterial metallothioneins listed in Table 7.

TABLE 7

Sequences of Some Known Bacterial Metallothionein Proteins

| Organism | Protein Name | Gene Locus | Sequence |
|---|---|---|---|
| Bacteria | | | |
| *Anabaena variabilis* ATCC 29413 | metallothionein, family 14 | Ava C0149 | MMLSMTTTVTQMKCACPSCLCVVSLTDAVIKDGKAYCGEECAN NHPNGQGCGHTGCDCQSNSLFPIHNSQLQSVVA |

TABLE 7-continued

Sequences of Some Known Bacterial Metallothionein Proteins

| Organism | Protein Name | Gene Locus | Sequence |
|---|---|---|---|
| Chlamydia trachomatis A/HAR-13 | metallothionein family protein | CTA_0140 | MSRKPASNSSRNTKRASDTSWEVIAQDYNKAVDRDGHFYHKE VILPNLLSKLHISRSSSLVDVGCGQGILEKHLPKHLPYLGIDLSPS LLRFAKKSASSKSRRFLHHDMTQPVPADHHEQFSHATAILSLQN MESPEQAIAHTANLLAPQGRLFIVLNHPCFRIPRLSSWLYDEPKK LLSRKIDRYLSPVAVPIVVHPGEKHSETTYSFHFPLSYWVQALSN HNLLIDSMEEWISPKKSSGKRARAENLCRKEFPLFLFISALKISK |
| Gloeobacter violaceus PCC7421 | metallothionein | gsl3430 | MTTVTQMKCACEACLCVVTLSEALEKDGKYFCSGPCANGHPD GSGCGHTGCECN |
| Pirellula sp. strain 1 | metallothionein MT-2 | NT02PS2904 | MMLRTSMMFAATVLIGVAILFATRSAISSDNASAQNGEACPCNQ CDVGCDCCVNGDVNCDNCSCEACECDACDTAASDFAVAKMS CCAGKTCENAANEKAASSDVLTSAVAAACVCGQCDADCNCCL DESVDCDNCSCEVCQCEGCVDAPATGA |
| Pseudomonas aeruginosa PAO1 | probable metallothionein | PA2140 | MNSETCACPKCTCQPGADAVERDGQHYCCAACASGHPQGEP CRDADCPCGGTTRPQVAEDRQLDDALKETFPASDPISP |
| Pseudomonas entomophila L48 | putative metallothionein | PSEEN2769 | MNEQRCACNHCSCTVDANAVVQDGKAYCCEACATGHRNGEP CRMADCKCGELTQPKESTVDNALDETFPASDPISP |
| Pseudomonas putida KT2440 | metallothionein, putative | PP_3262 | MNDQRCACTHCSCTVDANALQRDGKAYCCEACASGHRKGEP CRMQDCHCGEKPGESAVDNALDETFPASDPISP |
| Pseudomonas syringae pv B728a | metallothionein-related protein | NT04PS4737 | MAAGRRSGLSGQYDDAQACSAIGNTCTCTGGHARDTGKACCP ACGVTAACFTTFHCPGAYRWLVMFPGAMAGWSG |
| Staphylococcus epidermidis RP62A | metallothionein 2-related protein | SERP2224 | MEKCARPNCNCVLGETKVEEAGKVYCSQECVDNCTDEVCECK DCSCATA |
| Synechococcus elongatus PCC 6301 | SmtA metallothionein | syc0263_d | MTSTTLVKCACEPCLCNVDPSKAIDRNGLYYCSEACADGHTGG SKGCGHTSCNCHG |
| Synechococcus elongatus PCC 7942 | SmtA metallothionein | Synpcc7942_1290 | MTSTTLVKCACEPCLCNVDPSKAIDRNGLYYCSEACADGHTGG SKGCGHTGCNCHG |
| Synechococcus sp. CC9311 | bacterial metallo-thionein-related protein | GSYN0909 | MMNEVLLLCDCSLCKRSVEESRSIRIGGQHFCSESCAKGHPNM EPCDGERDGCNCGIAELELLLAAAD |
| Synechococcus sp. CC9311 | bacterial metallo-thionein-related protein | GSYN1173 | MTVTVVKCACSSCTCEVSSSSAISRNGHSYCSDACASGHRNNE PCHDAAGACGCNCGS |
| Synechococcus sp. CC9311 | bacterial metallo-thionein-related protein | GSYN2572 | MTTNLVRCDCPPCTCSIEEATAAMYGNKLFCSEACATAHINQEP SNSAEHTECSCGC |
| Thermosynechococcus elongatus BP-1 | metallothionein | tsl1016 | MTTVTQMKCACPHCLCIVSLNDAIMVNGKPYCSEVCANGTCKE NSGCGHAGCGCGSA |
| Mammals | | | |
| Homo sapiens | metallothionein 1G | MT1G | MDPNCSCAAAGVSCTCASSCKCKECKCTSCKKSCCSCCPVGC AKCAQGCICKGASEKCSCCA |
| Homo sapiens | metallothionein 1M | MT1M | MDPNCSCTTGVSCACTGSCKCKECKCTSCKKSCCSCCPVGCA KCAHGCVCKGTLEA |
| Homo sapiens | metallothionein 2A | MT2A | MDPNCSCAAGDSCTCAGSCKCKECKCTSCKKSCCSCCPVGCA KCAQGCICKGASDKCSCCA |
| Homo sapiens | metallothionein 4 | MT4 | MDPRECVCMSGGICMCGDNCKCTTCNCKTCRKSCCPCCPPG CAKCARGCICKGGSDKCSCCP |
| Canis lupus familiaris (beagle) | metallothionein 1F | MT1F | MDPDCSCSTGGSCTCAGSCKCKECKCTSCKKSCCSCCPVGCA KCAQGCICKGASDKCSCCA |
| Mus musculus | metallothionein 1 | Mt1 | MDPNCSCSTGGSCTCTSSCACKNCKCTSCKKSCCSCCPVGCS KCAQGCVCKGAADKCTCCA |
| Rattus norvegicus | metallothionein 1a | Mt1a | MDPNCSCSTGGSCTCSSSCGCKNCKCTSCKKSCCSCCPVGCS KCAQGCVCKGASDKCTCCA |
| Other | | | |
| Oryzias latipes (fungus) | metallothionein | LOC100049397 | MDPCDCSKTGKCNCGGSCTCTNCSCTSCKKSCCACCPSGCTK CASGCVCKGKTCD |

TABLE 7-continued

Sequences of Some Known Bacterial Metallothionein Proteins

| Organism | Protein Name | Gene Locus | Sequence |
|---|---|---|---|
| Caenorhabditis elegans | metallothionein | mtl-1 | MACKCDCKNKQCKCGDKCECSGDKCCEKYCCEEASEKKCCP AGCKGDCKCANCHCAEQKQCGDKTHQHQGTAAAH |
| Drosophila melanogaster | metallothionein A | MtnA | MPCPCGSGCKCASQATKGSCNCGSDCKCGGDKKSACGCSE |
| Zea mays (corn) | metallothionein1 | mtl1 | MSCSCGSSCGCGSSCKCGKKYPDLEETSTAAQPTVVLGVAPE KKAAPEFVEAAAESGEAAHGCSCGSGCKCDPCNC |
| Danio rerio (zebra fish) | metallothionein 2 | mt2 | MDPCECAKTGTCNCGATCKCTNCQCTTCKKSCCSCCPSGCSK CASGCVCKGNSCGSSCCQ |
| Xenopus laevis (African clawed frog) | metallothionein A | mt-A | MDPQDCKCETGASCSCGTTCSCSNCKCTSCKKSCCSCCPAEC SKCSQGCHCEKGSKKCSCCN |

To determine which proteins are most efficient at binding test metals, the bacterial constructs can be used to transform K12 *E. coli* using standard transformation protocols. Transformed clones are then selected by growing the bacteria in increasing levels of toxic metals to determine which DNA construct is most able to give the bacteria a selective advantage for each metal. This process can also be repeated using other types of bacteria such as cyanobacteria, which can be used in bioreactors suited for the specific conditions, although superior promoter and termination sequences would be used to control the DNA transcription in such circumstances. These could include the promoter and/or other regulatory sequences that flanked the genes in their native organisms.

Where non-bacterial cells will be used in the bioremediation process, the various metal sequestering genes should be converted into vectors so these genes are functionally linked to promoters and polyadenylation regions tailored for expression in the specific organism selected as the host. These should then be tested in the cell of choice to confirm the relative metal sequestering properties of these proteins.

Example 2

Improving Transcription of Metal Sequestering Proteins

To improve the transcription of the metal sequestering protein (or any other protein of interest), a construct can be created with the sequestering protein coding region linked to the DNA encoding a selectable marker such as β-lactamase (shown in FIG. 1B). These two separate genes are functionally or operably linked to a single promoter upstream of the sequestering protein and a single terminator downstream of the selectable marker (exemplified here as β-lactamase). This construct is used to transform bacteria that are grown in selection media with increasing concentrations of ampicillin and contaminating metals. The rate of cell growth is tracked along with the concentration of metal remaining in the media. As the concentration of ampicillin increases, the cells respond by transcribing more frequently from the β-lactamase gene. As this is downstream of the metal sequestering protein gene and both are driven by a single promoter, the metal sequestering protein gene will also be transcribed at a higher level.

Example 3

A Selectable Marker System Using Enzymes in the Vitamin B12 Pathway

Two cyanobacteria strains, *Synechococcus* sp. PCC 6911 and *Synechococcus* sp PCC 7335 are grown under normal conditions in their recommended ATCC medium in shaker flasks at 26° C. under light intensity of 2,000-3,000 lux. *Synechococcus* sp. PCC 6911 is grown in medium 616 (BG-11 medium for blue-green algae) and *Synechococcus* sp PCC 7335 (unable to produce its own Vitamin B12) is grown in medium 1047 (MN marine medium supplemented with 20 micrograms/L Vitamin B12). *Synechococcus* sp. PCC 6911 was isolated from lake water and *Synechococcus* sp PCC 7335 was isolated from a snail shell in an intertidal zone. Both are available from the ATCC. Normal growth curves for each bacterium are established through standard division and determination of optical density.

As multiple genomes from members of the *Synechococcus* family have been sequenced, the specific sequences of the enzymes in the Vitamin B12/cobalamin pathway in these two bacteria are determined by standard PCR amplification with specific and degenerative primers. Table 8 lists some of the potential target loci. Comparison of the genes in *Synechococcus* sp. PCC 6911 and *Synechococcus* sp PCC 7335 allows determination of the deleted enzyme(s) that prevent *Synechococcus* sp PCC 7335 from producing its own Vitamin B12. This information indicates targets in the *Synechococcus* sp. PCC 6911 bacteria with the greatest chance of becoming successful selection markers.

TABLE 8

Known Cobalamin Production Enzyme Loci in *Synechococcus* Bacteria.

| cbiB | cbiG/cobJ | cobD-1 | cobB | cobW | cobK |
| cobH | cobO-1 | cbiE/cbiT | cbiX | cobO-2 | cobD-2 |
| Cobs | cobI | cobQ | cobN | cobC | cobA |

Members of the oxygen dependent pathway have the prefix as "cb" whereas members of the oxygen independent pathway have the prefix "co."

Vitamin B12 enzyme loci are disrupted in *Synechococcus* sp. PCC 6911 bacteria by targeted integration using standard techniques. Plasmids are created that contain between 0.3 and 3 kb of DNA homologous to DNA flanking the target enzyme locus. A functional gene for antibiotic resistance (e.g., resistance to tetracycline) is inserted between the two ends of the disrupted Vitamin B12 locus (FIG. 2A and FIG. 2B). The plasmids are linearized, taking care to remove the origin of replication to prevent intact plasmid transformation, and used to transform the *Synechococcus* sp. PCC 6911 bacteria by either lipid or electrical transformation. Linear DNA can also be created by PCR amplification of the desired section of DNA. Selection is conducted in ATCC 616 media supplemented with Vitamin B12 and the antibiotic tetracycline.

Surviving clones are retested to find those that cannot grow on tetracycline plates without the Vitamin B12 supplement. Single colonies that survive these growth conditions are tested by PCR amplification to determine correct gene disruption (FIG. 2C). This PCR amplification is conducted by using one primer within the introduced DNA and one within the host DNA. Only those with correct integration will give correct PCR products. Once the desired clone is determined (to be referred to as the Knock-Out or KO clone), it can be maintained with media containing Vitamin B12 but will no longer need tetracycline selection. As some organisms have two pathways to produce Vitamin B12 (oxygen-dependent or oxygen-independent), the alternative pathway is also disrupted, when present, with a construct containing a different antibiotic. An overview of the targeted disruption (or Knock-Out) procedure along with diagrams of the constructs is shown in FIG. 2A-FIG. 2C).

The early steps in restoring Vitamin B12 production to the KO clone include creating vector constructs (e.g., plasmids) with the functional genes. For quality control, the locus in the plasmid can encode an enzyme with an amino acid sequence (preferred methods) or homologous amino acid sequence but identical enzyme function but contain a slightly different nucleotide sequence. Plasmid constructs are tested in the KO clone by standard intact plasmid transformation and selection in media with no added Vitamin B12 and no antibiotics. This experiment allows the testing of the replacement loci with minimal effort.

To create DNA constructs for reinsertion into the disrupted locus, genes successful in previous plasmid transformation experiments are combined with the 0.3 and 3 kb of DNA flanking sequence that was used in the original gene disruption experiment (FIG. 3A and FIG. 3B). These DNA constructs are linearized by digestion or PCR amplification and used to transform the KO clone. Potential clones are isolated by their ability to survive without Vitamin B12 supplementing the media and their inability to survive in the presence of tetracycline. Their DNA is tested by PCR amplification to determine clones with correct integration (FIG. 3C). These are referred to as knock-in (or KI) clones.

To test the ability of the Vitamin B12 enzyme to serve as a selection marker, genes for proteins of interest are incorporated into constructs for use in Knock-in experiments. The proteins of interest genes can be functionally or operationally linked to their own promoter and/or terminator sequences or placed under the control of the same regulatory sequences that control the expression of the gene encoding the Vitamin B12 enzyme. The genes for proteins of interest, which we may also refer to as engineered protein genes, can be metal-binding proteins or any other enzyme or protein desired in an environmental, industrial, or therapeutic process. Successful knock-in reactions can be determined by screening the clones for production of the selection marker (here, a Vitamin B12 synthetic enzyme) and the engineered protein (here, a metal-binding protein). If desired, preliminary experiments are conducted by standard plasmid transformation to evaluate the engineered construct without the added effort of selecting for a successful knock-in reaction. Although this is an easier reaction, loci that have integrated into the bacterial chromosome will tend to have improved genetic stability when compared to a locus on a separate plasmid. An overview of the targeted insertion (or knock-in) procedure along with diagrams of the necessary constructs is shown in FIG. 3A-3C.

Example 4

Tagged Metal Sequestering Proteins

To more easily isolate the metal sequestering protein from host cells, lysates, solutions and so forth (and to thus isolate the contaminating metal), a recombinant protein can be engineered to include the metal sequestering protein and a protein tag. In this example, the tag is maltose-binding protein (MBP) but other tags can be used depending on the desired purification protocol. As in Example 2, the tagged metal sequestering protein and the selection marker are functionally linked to a single promoter/terminator system to improve transcription of the tagged metal sequestering protein (shown in FIG. 4A). As in Example 2, the construct is used to transform bacteria that are grown in increasing concentrations of ampicillin (if using the β-lactamase gene) and contaminating metals. In addition to sequestering the metal within the cells, the tagged protein will continue to concentrate metal even after its release from the cell.

The tagged metal sequestering protein along with its bound metal can be isolated by passing the growth media or ruptured cells over an amylose column. The MBP will bind to the amylose, retaining the metal/protein combination and the remaining material can be washed away. The retained protein is then treated to release the metal into a small volume.

Example 5

Creating a Single Protein Containing a Tagged Metal Sequestering Domain and a Domain that Allows Growth in Selection Media To more tightly link the production of the tagged metal sequestering protein with selection, the two proteins are linked by a flexible hinge. The termination codon from the tagged metal sequestering protein coding gene and the start codon from the .beta.-lactamase gene or other selectable marker such as an enzyme in the Vitamin B12 pathway are deleted. In between these two genes, the DNA encoding an amino acid hinge is inserted (shown in FIG. 6). Many different sequences could be used, but in this example the hinge has the sequence GGGGSGGGGSGGGGS. When translated, the tagged protein has a domain that sequesters metal and a domain that allows growth in ampicillin or other selectable media. The flexibility between the two domains will minimize the amount of interference between the respective proteins' functions. This construct can be tested by the same process described in Example 4.

Example 6

Isolating Metal-Binding Transcription Factors and Paired Promoters

As part of the process of developing improved metal sequestering proteins (described in Example 1), transcription factors that require a metal cofactor will also be isolated. These frequently contain zinc finger-like domains that use the metal ion to stabilize their configuration. Without the correct configuration created by the metal co-factor, they are less able to bind to their promoter region DNAs and trigger transcription. Their coding RNA and genomic DNA sequences are also isolated by the method described in Example 1. As not only the transcription factor protein but also the matched DNA promoter region is needed, purified protein is created for DNA binding studies. The transcription factor genes are introduced into a standard bacterial protein expression system and the transcription protein is purified. As much as possible, the production and purification should be carried out in conditions of low metal. Once the protein is purified, it is mixed with an excess of the target metal. The transcription factors with their desired metal co-factors are then used in standard techniques including DNase footprinting assays.

To test the transcription factor and promoter combination, a vector is created that has two expression units (as shown in FIG. 7). The first unit includes DNA encoding the transcription factor requiring metal cofactor (mTF) with an operational promoter and terminator. The second unit includes DNA encoding the selectable marker functionally linked to a promoter bound by the mTF and a terminator. This creates a selectable marker whose expression is controlled by a transcription factor that does not function unless it can obtain the necessary metal co-factor. In this system, the production of the transcription factor is under ubiquitous control but the protein required for cell survival can only be produced if the transcription factor is able to obtain appropriate metal so it can functionally fold. This functionally folded factor can then bind to its specific promoter region and start the transcription of the second gene that confers cell survival.

To test the ability of the transcription factor to obtain metal from the solution, bacterial cells are transformed with the combination vector and then grown in ampicillin-positive selection media with altering metal concentrations. The growth of bacteria is followed and the media is tested by chemical means to follow the depletion of added metal. The ideal will be the combination that allows rapid growth during the early phase when the metal concentration is highest but then drops when the metal is depleted.

If so desired, a molecular tag can be added to the transcription factor construct so this protein can also be more easily removed from the cells for greater metal purification.

Example 7

Tagged Metal Sequestering, Selectable Marker Proteins Under the Control of a Transcription Factor Requiring a Metal Cofactor (mTF)

Figure 4D:
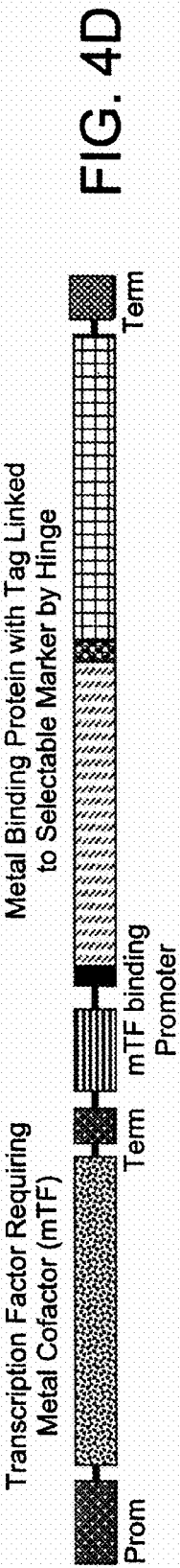
FIG. 4D is a schematic diagram of an expression cassette containing a promoter and a terminator that regulate the expression of an mTF and an mTF-binding promoter and a second terminator to regulate the expression of a sequence encoding a tagged metal-binding protein, a hinge, and a selectable marker.
Figure 8:
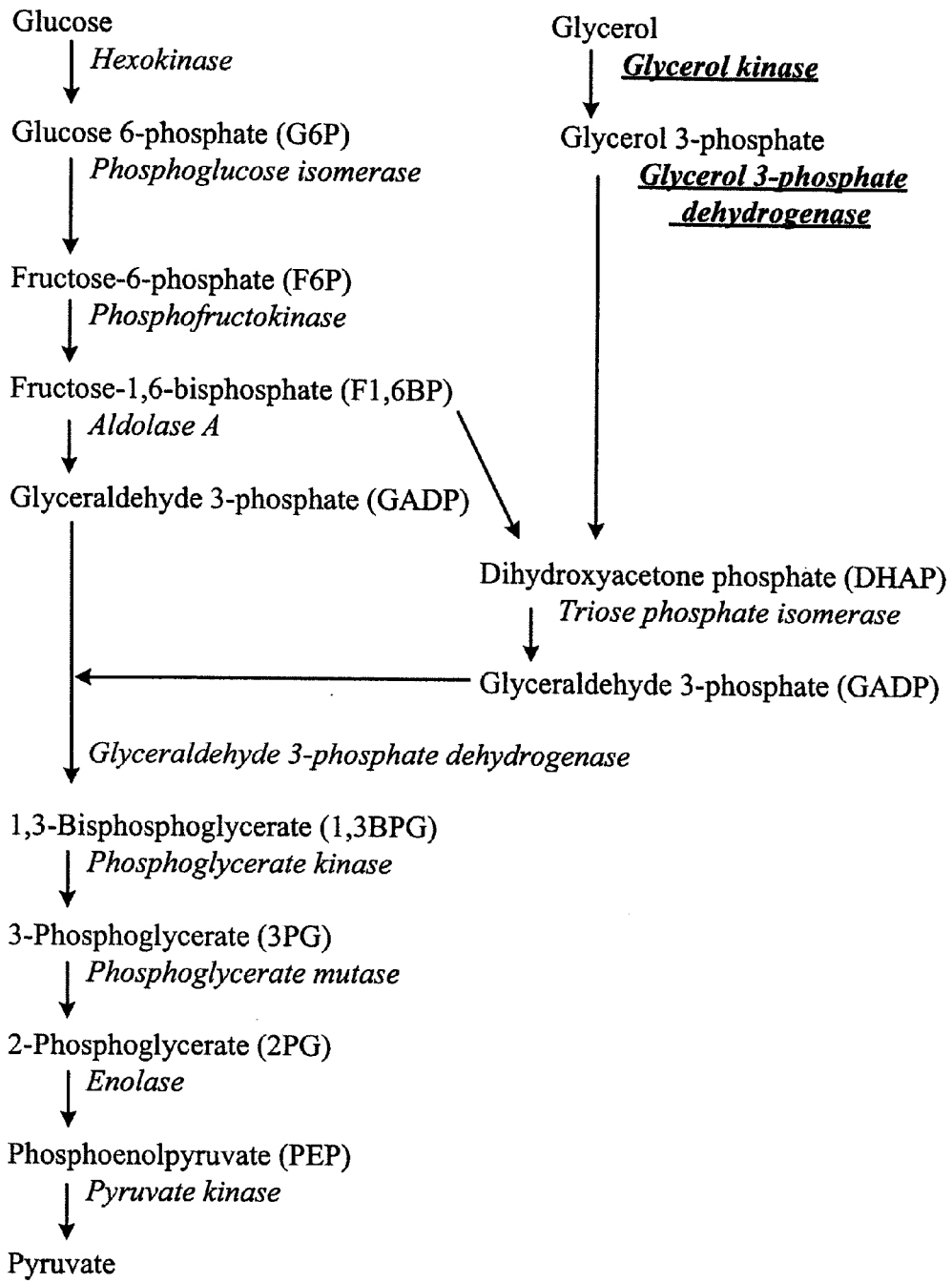
FIG. 8 is a schematic diagram of the glycolysis pathway, showing enzymes (underlined) that can be used to transfer glycerol into the pathway.
Figure 9:
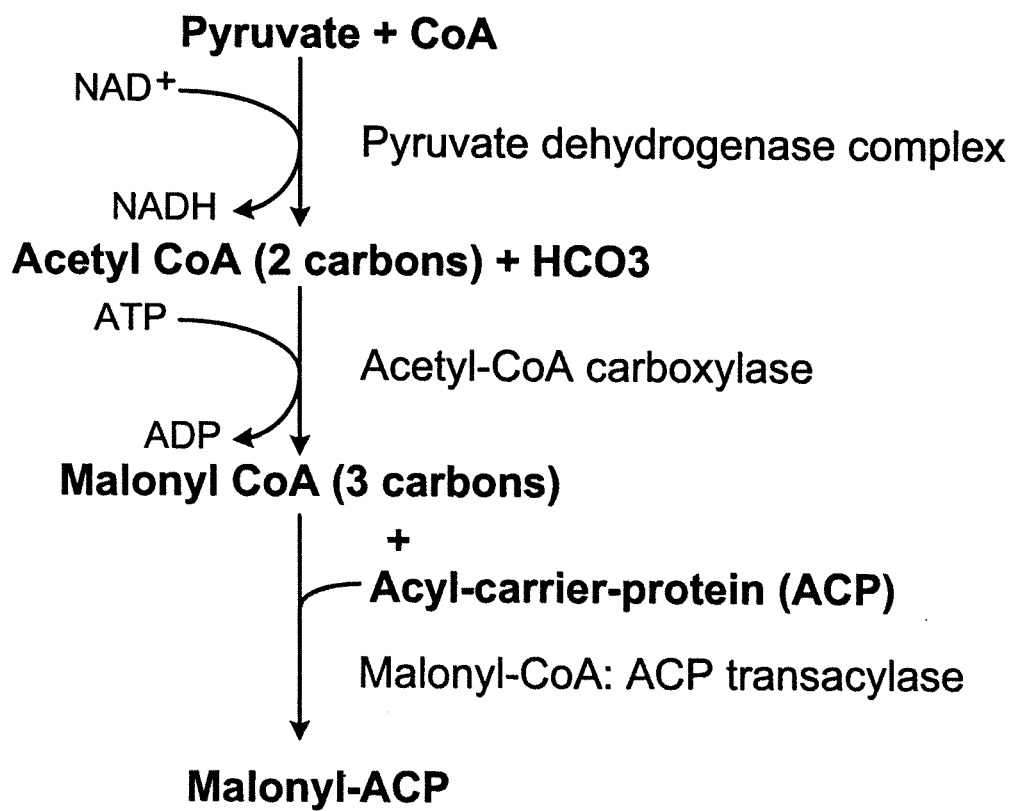
FIG. 9 is a schematic diagram of the initiation of fatty acid chain production.
Figure 10:
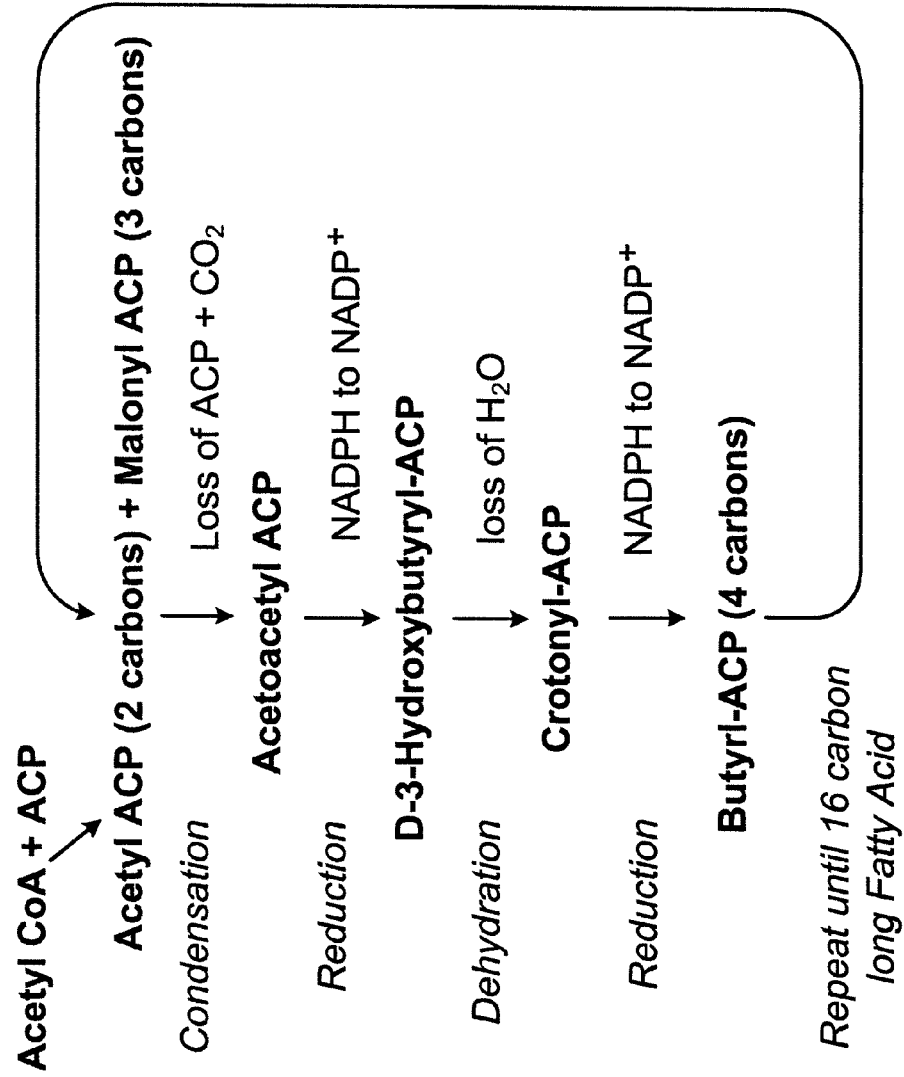
FIG. 10 is a schematic diagram of the sequence of reactions to extend fatty acid chain.
Figure 11:
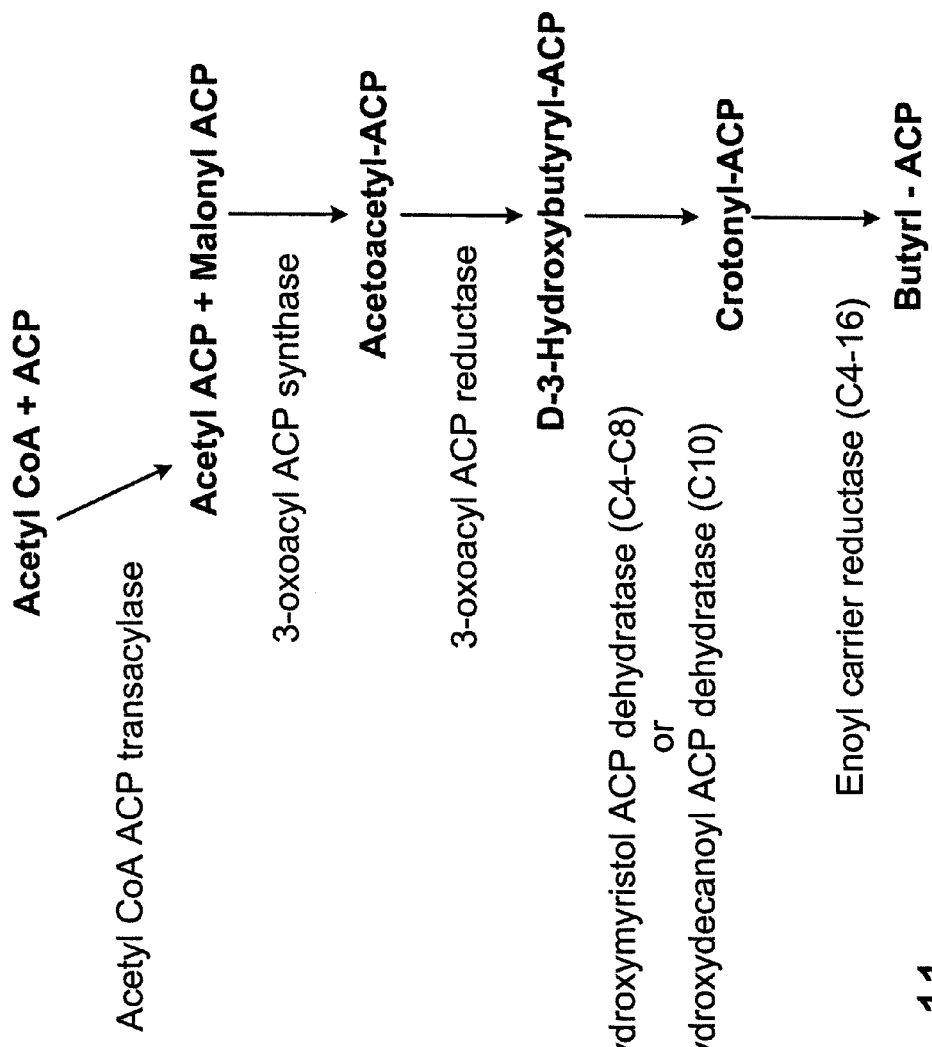
FIG. 11 is a schematic diagram of fatty acid biosynthesis in bacteria, showing the bacterial enzymes that are involved.
Figure 12:
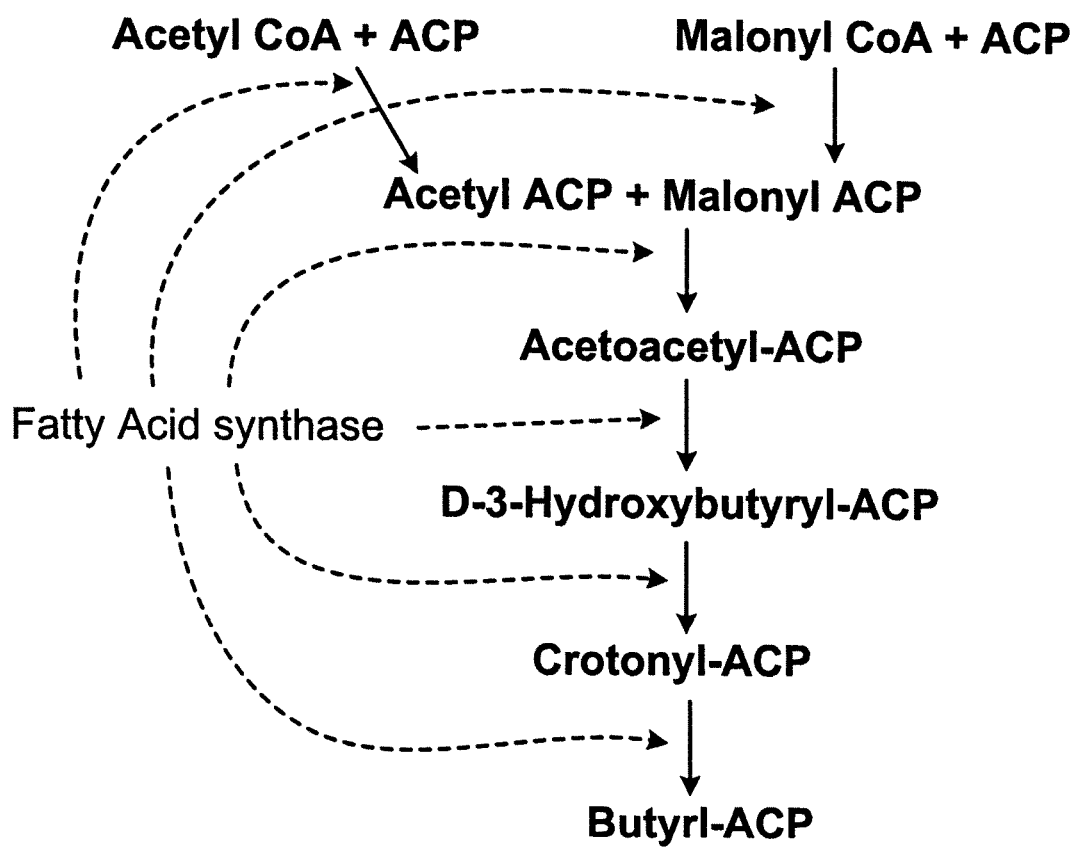
FIG. 12 is a schematic diagram of fatty acid biosynthesis in eukaryotes, illustrating the reactions catalyzed by Fatty Acid Synthase, a complex enzyme.
Figure 13:
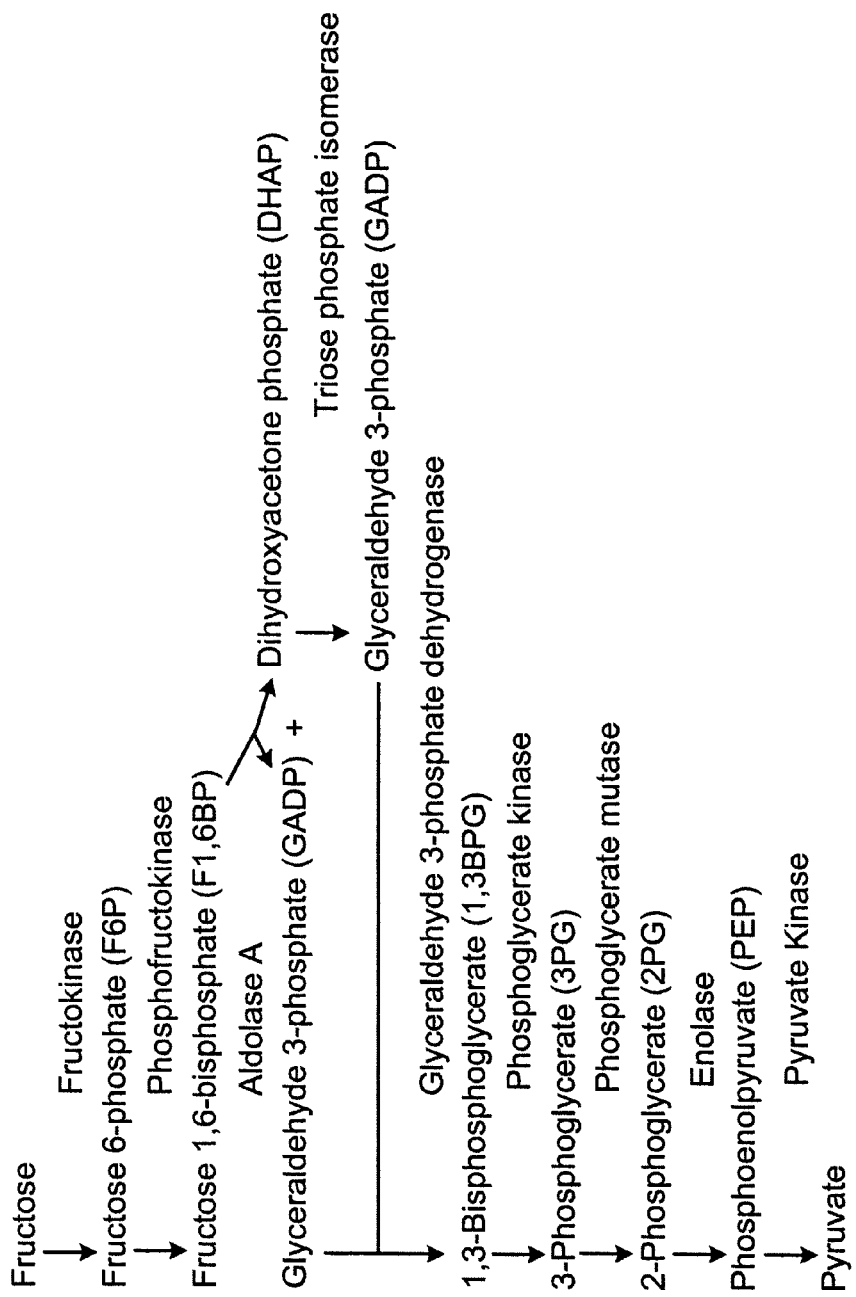
FIG. 13 is a schematic diagram of cyanobacteria metabolism of Fructose to Pyruvate.
Figure 14:
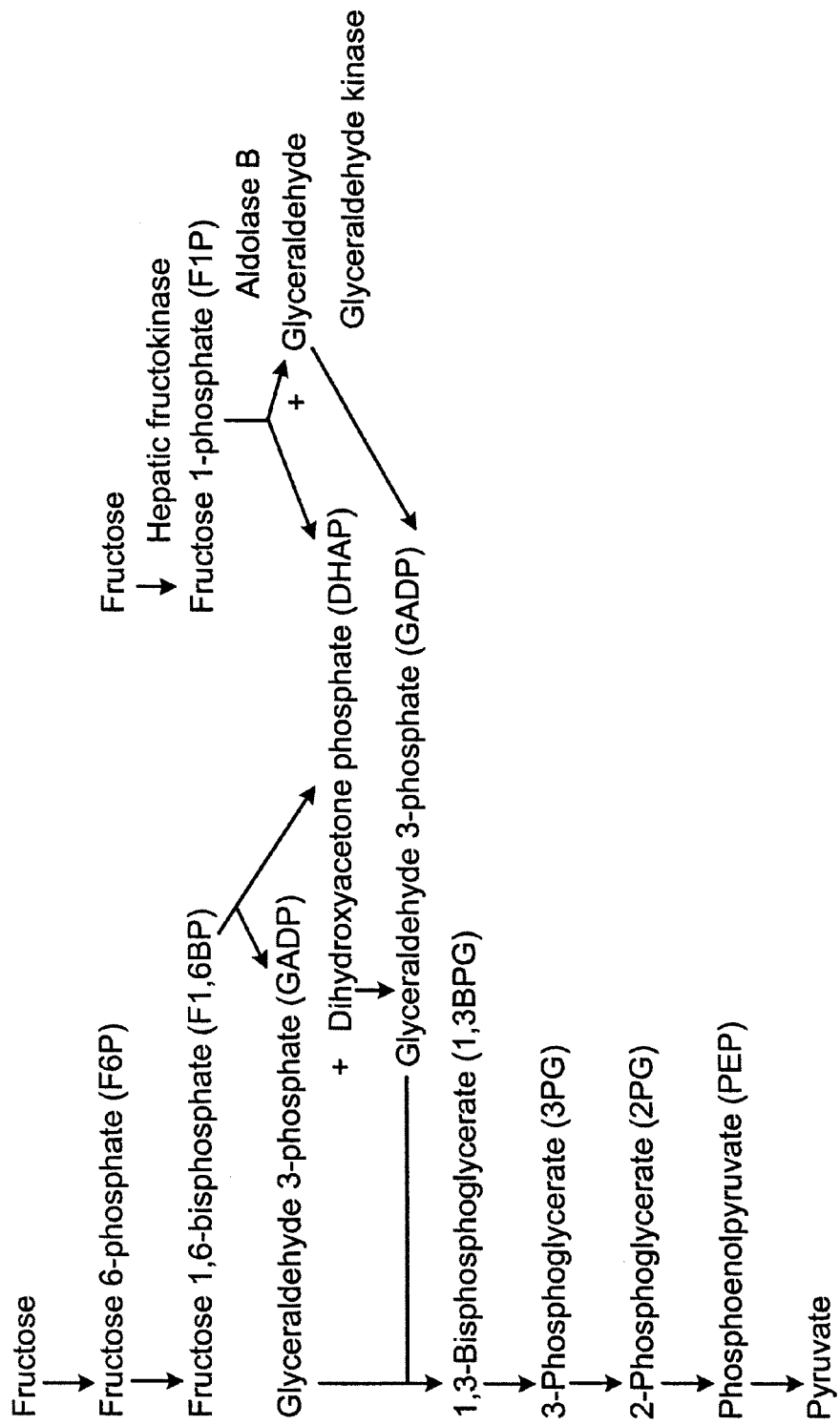
FIG. 14 is a schematic diagram of cyanobacteria metabolism of Fructose to Pyruvate, showing enzymes that can be added to increase the rate of metabolism.
Figure 15:
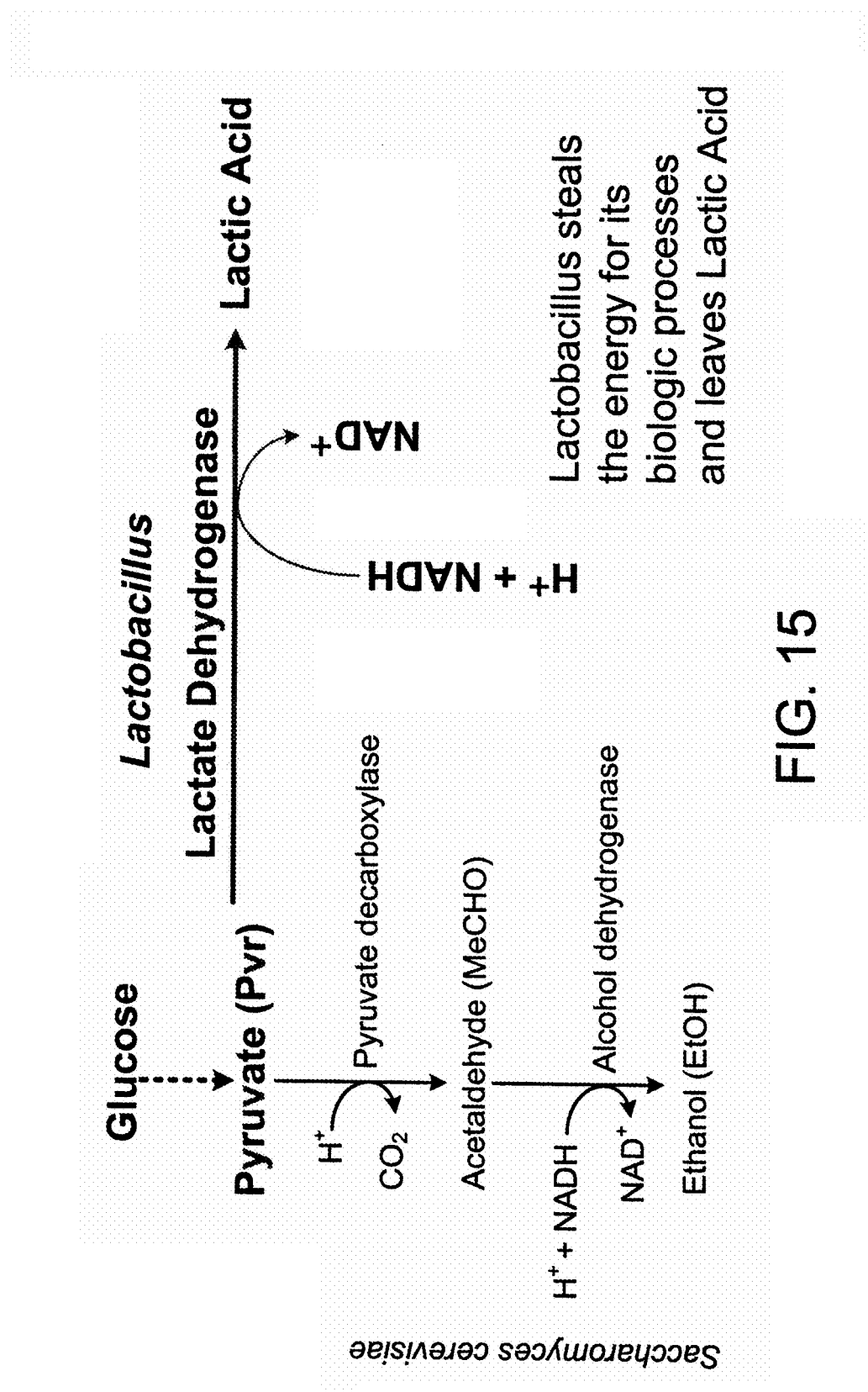
FIG. 15 is a schematic diagram of anerobic fermentation using *S. cerevisiae* resulting in the production of ethanol from glucose and illustrating how lactate dehydrogenase produced by contaminating *Lactobacillus* subverts pyruvate to the production of lactic acid.
Figure 16:
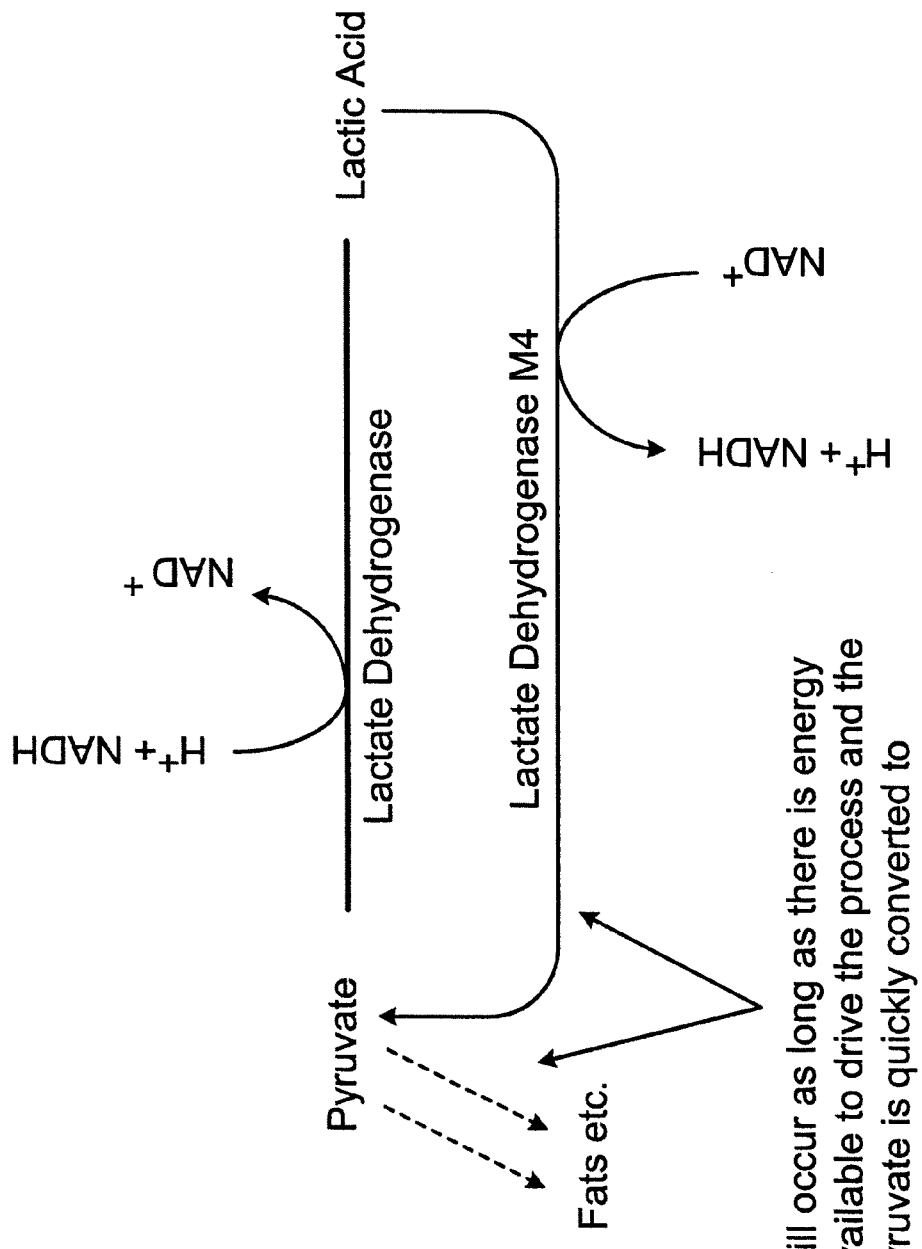
FIG. 16 is a schematic diagram of how mammalian lactate dehydrogenase can convert lactic acid back to pyruvate.
Figure 17:
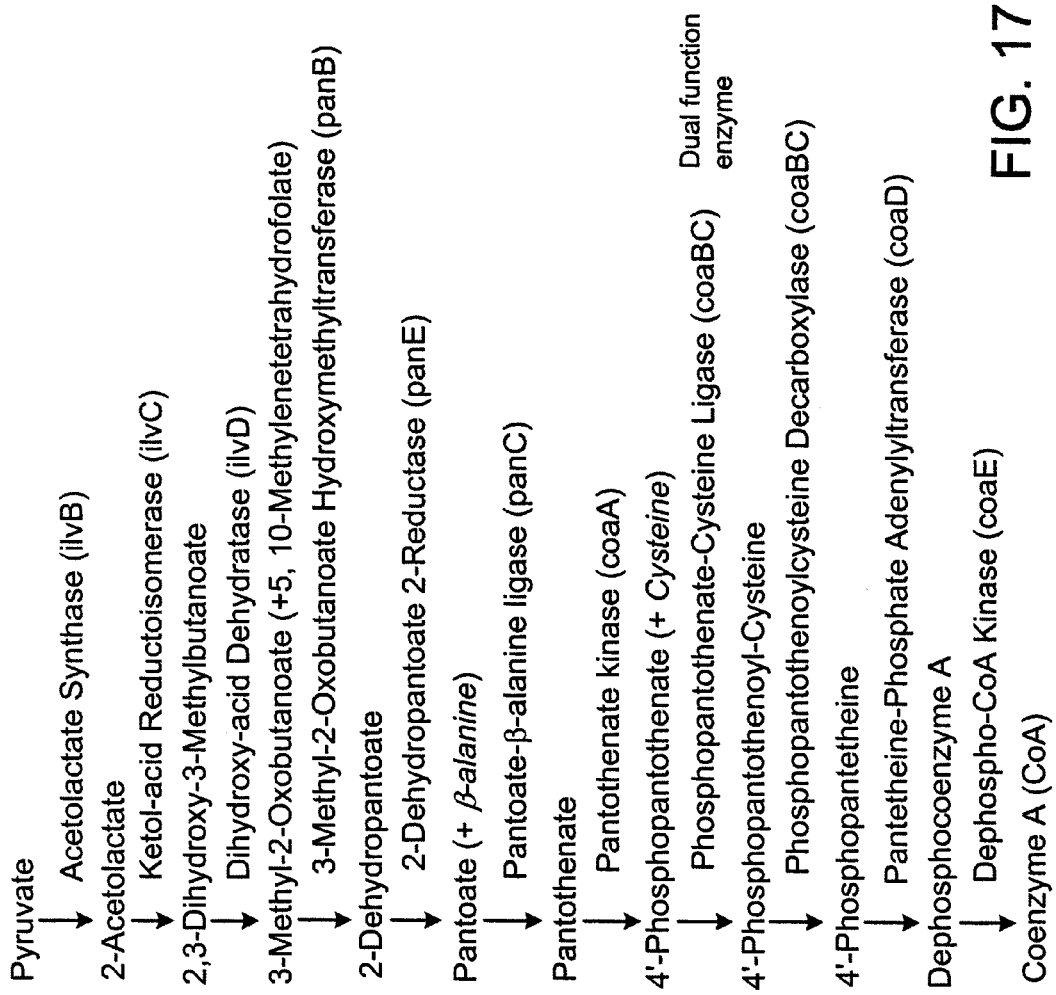
FIG. 17 is a schematic diagram of a pyruvate metabolic pathway.
Figure 18:
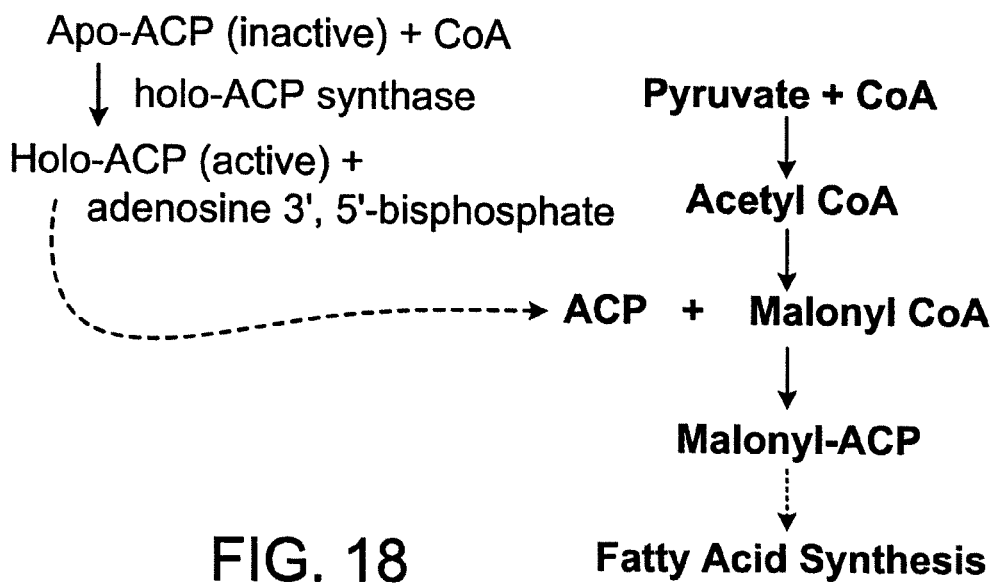
FIG. 18 is a schematic diagram of fatty acid synthesis and the involvement of activating Acyl-Carrier Protein (ACP).

To put the cells under high pressure to obtain metals while rapidly sequestering those metals for later purification, we have created a vector in which a tagged metal sequestering, selectable marker protein (described in Example 5) is placed under the control of the mTF promoter (described in Example 6). The construct for the mTF functional linked to another promoter/termination set is also included (shown in FIG. 4D). This results in a process that includes the transcription factor that requires a metal being produced to initiate the transcription of the combined metal sequestering, selection marker protein.

Using the methods described in Examples 5 and 6, cells are created and tested. In this system, the cells rapidly deplete the media of metal because they need a metal co-factor for the transcription factor to produce the protein for survival in the selection media. As proteins allowing survival also bind metal, excess metal-binding capacity is created and any metal freed from the transcription factor will be quickly bound by protein that can be isolated easily. The interlocking processes will result in the rapid reduction of metal concentrations to very low levels.

Example 8

Using Isolated Tagged Protein to Purify Metal from Solution

Metals can be purified from any of the cells that have been created in Examples 4, 5, 6 and 7 that include tagged metal-binding proteins either as transcription factors or metal sequestering proteins. To purify the metal, the cells can be grown under conditions favorable for efficient metal isolation. These include growth in media with reduced levels of manganese (Mn), zinc (Zn), molybdenum (Mo), copper (Cu) and cobalt (Co) but elevated levels of lead or cadmium. The cells are allowed to grow to completion and harvested by centrifugation. The media that will contain debris from cells that died during the growth process are passed over a selection column of amylase to bind all MBP-tagged protein. The concentrated cells are lysed and their protein fraction is also run over an amylase selection column. The columns are washed to remove debris and then stripped in a small volume to remove the metal-binding proteins. The metals are then stripped from the proteins by chemical means and isolated away from the small amount of biologic debris.

Example 9

Development of Cells and Means of Use

The DNA constructs described in the previous examples can be used in many conditions and with many cell types depending on the desired bioremediation conditions or other application. For the most efficient transcription process, the promoter and termination (or polyadenylation) sequences are tailored for most efficient expression in the desired subject cells. The mTF promoter region is not changed. The selectable marker and protein tags are also altered to better fit the cell type, desired growth conditions and desired protein purification conditions. The desired cell type is transformed or transfected with the tailored vector and grown in conditions with the selectable marker and sufficient concentrations of the desired metal to be isolated. The cells are then transferred into a vessel with the material to be cleaned with all necessary nutrients except for the metal to be isolated. The cell growth and metal-binding protein production in encouraged by frequently replenishing the non-metal nutrients. The cells are harvested and the metal-binding proteins and bound metals are purified.

This process can be conducted in a single vessel or a series of vessels with cells with similar or different metal isolating characteristics. The material to be cleaned could be a liquid, gas or solid material depending on the conditions of the cell growth. The process could also be adapted for more complex organisms such as intact plants.

What is claimed is:

1. A recombinant genetically modified bacterial cell comprising:
 a recombinant chromosomally integrated expression cassette, the recombinant chromosomally integrated expression cassette comprising a first nucleic acid molecule encoding a protein of interest and a second nucleic acid molecule encoding a positive selectable marker, said positive selectable marker being an enzyme necessary for the production of an essential vitamin B12, which is the enzyme with EC 1.3.1.54 or EC 2.1.1.133, wherein the expression of the positive selectable marker is necessary for survival of the genetically modified bacterial cell in media lacking said vitamin, and wherein promoter of the expression cassette drives expression of positive selectable marker and expression of the protein of interest.

2. The recombinant genetically modified bacterial cell of claim 1, wherein the cell is a cyanobacterium.

3. The recombinant genetically modified bacterial cell of claim 2, wherein the cyanobacterium is *Anabaena* species (sp), *Anabaenopsis* sp, *Aphanizomenon* sp, *Arthrospira* sp,

*Calothrix* sp, *Chamaesiphon* sp, *Chlorogloeopsis* sp, *Chroococcidiopsis* sp, *Chroococcus* sp, *Cyanothece* sp, *Cylindrospermum* sp, *Dactylococcopsis* sp, *Dermocarpella* sp, *Fischerella* sp, *Geitlerinema* sp, *Gloeobacter* sp, *Gloeocapsa* sp, *Gloeothece* sp, *Leptolyngbya* sp, *Lyngbya* sp, *Microchaete* sp, *Microcoleus* sp, *Microcystis* sp, *Myxosarcina* sp, *Nodularia* sp, *Nostoc* sp, *Oscillatoria* sp, *Pleurocapsa* sp, *Pseudanabaena* sp, *Scytonema* sp, *Spirulina* sp, *Stanieria* sp, *Symploca* sp, *Synechococcus* sp, *Synechocystis* sp, *Tolypothrix* sp, or *Xenococcus* sp.

4. The recombinant genetically modified bacterial cell of claim 1, wherein the protein of interest is a metal-binding protein.

5. The recombinant genetically modified bacterial cell of claim 4, wherein the metal-binding protein is selected from the group consisting of a metallothionein and a transcription factor.

6. The recombinant genetically modified bacterial cell of claim 1, wherein the protein of interest is a protease, an oxidase, a phytase, a chitinase, an invertase, a lipase, a cellulase, a xylenase, a kinase, or a phosphatase.

7. The recombinant genetically modified bacterial cell of claim 1, wherein the enzyme is pyruvate dehydrogenase, dihydrolipoyl dehydrogenase, dihydrolipoyllysine-residue acetyltransferase, acteyl-CoA carboxylase, malonyl-CoA: ACP transacylase or fatty acid synthase.

8. The recombinant genetically modified bacterial cell of claim 1, wherein the recombinant expression cassette further comprises a nucleic acid molecule encoding a purification tag operatively coupled to the first nucleic acid molecule.

9. The recombinant genetically modified bacterial cell of claim 1, wherein the recombinant expression cassette further comprises a nucleic acid molecule encoding a linker between the protein of interest and the selectable marker protein, wherein said linker acts as a hinge and wherein said protein of interest and the selectable marker enzyme retain biological activity.

10. The recombinant genetically modified bacterial cell of claim 1, wherein the protein of interest is a lipase.

11. A kit comprising the bacterial cell of claim 1 and instructional materials.

* * * * *